(12) United States Patent
Hollstien

(10) Patent No.: US 9,113,844 B2
(45) Date of Patent: Aug. 25, 2015

(54) NON-INVASIVE IMPLANT RUPTURE DETECTION SYSTEM

(76) Inventor: David S. Hollstien, Templeton, CA (US)

(*) Notice: Subject to any disclaimer, the term of this patent is extended or adjusted under 35 U.S.C. 154(b) by 1087 days.

(21) Appl. No.: 12/958,255

(22) Filed: Dec. 1, 2010

(65) Prior Publication Data

US 2011/0098576 A1 Apr. 28, 2011

Related U.S. Application Data

(60) Provisional application No. 61/265,741, filed on Dec. 1, 2009.

(51) Int. Cl.
*A61B 6/00* (2006.01)
*A61B 5/00* (2006.01)
(Continued)

(52) U.S. Cl.
CPC ............ *A61B 5/686* (2013.01); *A61B 5/0064* (2013.01); *A61B 5/0082* (2013.01); *A61B 5/0084* (2013.01); *A61B 5/4851* (2013.01); *A61B 19/24* (2013.01); *A61B 2562/08* (2013.01);
(Continued)

(58) Field of Classification Search
CPC .. A61B 2562/08; A61B 5/0084; A61B 5/686; A61B 2560/0276; A61B 2560/0462; A61B 5/4851; A61B 19/00; A61B 19/24; A61B 5/0059; A61B 5/0064; A61B 5/4312; A61B 2017/00796; A61F 2/12; A61F 2002/523; A61F 2210/0057; A61F 2/52; A61F 2240/00; A61F 2240/002; A61F 2240/008; A61F 2250/0003; A61F 2250/0058; A61F 2250/0071; A61F 2310/00005; A61F 2310/00; A61M 2210/1007; G02B 1/00
See application file for complete search history.

(56) References Cited

U.S. PATENT DOCUMENTS 4,795,463 A * 1/1989 Gerow .............................. 623/8
5,237,638 A * 8/1993 Narcisco, Jr. ................. 385/123
(Continued)

FOREIGN PATENT DOCUMENTS

WO WO 2006/135857 12/2006
WO WO 2008/014283 1/2008
(Continued)

OTHER PUBLICATIONS

Harold et al., Variability in the Properties of Silicone Gel Breast Implants, Division of Plastic and Reconstructive Surgery, Washington University of Medicine, and the Department of Mechanical Engineering and Chemical Engineering, pp. 647-655, Oct. 20, 2000, Washington University.

(Continued)

*Primary Examiner* — Amanda Lauritzen Moher
(74) *Attorney, Agent, or Firm* — Levine Bagade Han LLP

(57) ABSTRACT

Devices and methods for non-invasive implant rupture detection are described herein. Some variations of a non-invasive implant rupture detection device comprise a single optical waveguide, such as a silicone fiber, embedded in the shell of the implantable device where one end of the optical waveguide is connected to a photo emitter and the other end of the waveguide is connected to photo detector. An optical signal successfully transmitted from the photo emitter through an intact optical waveguide to the photo detector indicates that the implant shell is intact, while an optical signal that is transmitted by the photo emitter, but not detected by the photo detector, indicates that there is a discontinuity or rupture in the shell. The status of the implant shell is wirelessly communicated to an external reader and provided to a patient and/or a practitioner.

10 Claims, 15 Drawing Sheets

(51) Int. Cl.
   A61F 2/52    (2006.01)
   A61B 19/00   (2006.01)
   A61F 2/12    (2006.01)
(52) U.S. Cl.
   CPC ... A61F 2/12 (2013.01); A61F 2/52 (2013.01); A61F 2002/523 (2013.01)

(56) References Cited

U.S. PATENT DOCUMENTS

| | | | |
|---|---|---|---|
| 5,423,334 | A | 6/1995 | Jordan |
| 5,496,367 | A | 3/1996 | Fisher |
| 5,766,234 | A | 6/1998 | Chen et al. |
| 5,800,478 | A | 9/1998 | Chen et al. |
| 5,833,603 | A | 11/1998 | Kovacs et al. |
| 6,094,517 | A | 7/2000 | Yuuki |
| 6,187,043 | B1 | 2/2001 | Ledergerber |
| 6,332,093 | B1 | 12/2001 | Painchaud et al. |
| 6,723,932 | B2 | 4/2004 | Ohki et al. |
| 6,755,861 | B2 | 6/2004 | Nakao |
| 6,802,861 | B1 | 10/2004 | Hamas |
| 6,826,948 | B1 | 12/2004 | Bhatti et al. |
| 6,836,029 | B2 | 12/2004 | Greenberg |
| 6,855,143 | B2 | 2/2005 | Davison et al. |
| 7,158,707 | B2 | 1/2007 | Will et al. |
| 7,184,820 | B2 | 2/2007 | Jersey-willuhn et al. |
| 7,334,561 | B2 | 2/2008 | Neunteufl et al. |
| 7,575,596 | B2 | 8/2009 | Bowman et al. |
| 7,712,674 | B1 | 5/2010 | Warner et al. |
| 8,066,780 | B2 | 11/2011 | Chen et al. |
| 8,070,807 | B2 * | 12/2011 | Chen ............................ 623/8 |
| 2001/0033406 | A1 * | 10/2001 | Koike et al. ................. 359/152 |
| 2004/0162613 | A1 | 8/2004 | Roballey |
| 2005/0149186 | A1 | 7/2005 | Roballey et al. |
| 2005/0159646 | A1 | 7/2005 | Nordstrom et al. |
| 2006/0111632 | A1 | 5/2006 | Chen |
| 2006/0111777 | A1 * | 5/2006 | Chen ............................ 623/8 |
| 2006/0161266 | A1 | 7/2006 | Schwibner et al. |
| 2007/0135916 | A1 | 6/2007 | Maxwell et al. |
| 2007/0185575 | A1 | 8/2007 | Purkait |
| 2007/0186642 | A1 | 8/2007 | Sano |
| 2008/0054408 | A1 | 3/2008 | Tippey |
| 2008/0239321 | A1 | 10/2008 | Chen et al. |
| 2008/0269664 | A1 | 10/2008 | Trovato et al. |
| 2009/0012372 | A1 * | 1/2009 | Burnett et al. ............... 600/300 |
| 2009/0043385 | A1 | 2/2009 | Hamilton |
| 2009/0082644 | A1 | 3/2009 | Li |
| 2010/0060431 | A1 | 3/2010 | Stevenson et al. |
| 2010/0122904 | A1 * | 5/2010 | Hassibi et al. ............ 204/403.01 |
| 2011/0098576 | A1 | 4/2011 | Hollstein |
| 2012/0302874 | A1 * | 11/2012 | Hollstien ..................... 600/424 |

FOREIGN PATENT DOCUMENTS

| | | |
|---|---|---|
| WO | WO 2008/055229 | 5/2008 |
| WO | WO 2011/068906 | 6/2011 |

OTHER PUBLICATIONS

Bengtson et al., Style 410 Highly Cohesive Silicone Breast Implant Core Study Results at 3 Years, DOI 10.1097/01.prs.0000286666.29101.11, Plastic Surgery Associates and Medical Education Research Center; the Perkins Van Natta Center Cosmetic Surgery and Medical Skincare; Allergan Inc; and the Department of Plastic Surgery, pp. 40S-48S, 2007, Vanderbilt University School of Medicine.
Heden et al., Style 410 Cohesive Silicone Breast Implants: Safety and Effectiveness at 5 to 9 Years after Implantation, DOI: 10.1097/01.prs.0000239457.17721.5d, The Department of Plastic Surgery, Akademikliniken Hospital; Department of Radiology, Karolinska University Hospital; and Inamed Corporation, pp. 1281-1287, 2006, The American Society of Plastic Surgeons.
Norris et al., Silicone Materials for Optical Applications, Dow Corning, 6 pages, 2003, Midland, MI, US.
Collis et al., Magnetic Resonance Imaging and Explanation Investigation of Long-Term Silicone Gel Implant Integrity, The Royal Victoria Infirmary, Glasgow Royal Infirmary, Blackburn Royal Infirmary, and Bradford Royal Infirmary, DOI: 10.1097/01.prs.0000279374.99503.89, pp. 1401-1406, 2007, The American Society of Plastic Surgeons.
Rothmaier et al., Textile Pressure Sensor Made of Flexible Plastic Optical Fibers, Sensors vol. 8, ISSN 1424-8220, www.mdpi.org/sensors, pp. 4318-4329. 2008, Molecular Diversity Preservation International, Basel, Switzerland.
Spear et al., Inamed Silicone Breast Implant Core Study Results at 6 Years, The Department of Plastic Surgery, Georgetown University Hospital, and Allergan, Inc., DOI: 10.1997/01.prs.0000286580.93214.df, pp. 8S-16S, 2007, The American Society of Plastic Surgeons.
Dow Corning Photonics, Dow Corning, 7 pages, 2003, Dow Corning Corporation, Midland, MI, US.
Degroot, Jr. et al., Highly Transparent Silicone Materials, Dow Corning, 5 pages, 2005, Dow Corning Corporation, Midland, MI, US.
Maxwell, G. Patrick, MD, Evolution of Silicone Gel-Filled Breast Implants, p. 27, PlasticSurgeryProductsOnline.com, Aug. 2007.

* cited by examiner

NON-INVASIVE IMPLANT RUPTURE DETECTION SYSTEM

CROSS-REFERENCE TO RELATED APPLICATIONS

This application claims benefit under 35 U.S.C. §119(e) to U.S. Provisional Application Ser. No. 61/265,741, filed on Dec. 1, 2009, which is hereby incorporated by reference in its entirety.

BACKGROUND

Various devices may be implanted in a patient for therapeutic and/or cosmetic purposes. Examples of implantable devices include hip replacement devices, spinal support devices, cardiac devices such as pacemakers, and breast prosthetic devices. Such devices may be made of biocompatible materials, and to the extent that electronic components are included, at least a portion of the implantable device may be encased in a shell or casing.

Because the prosthetic devices are implanted in the body of a patient, it may be difficult to determine the condition of the device. For example, without direct access to an implanted device, it may be difficult to determine if the integrity of the shell or casing of the device is compromised. Therefore, devices and methods that may be used to confirm the integrity of the implant shell may be desirable.

BRIEF SUMMARY

Devices and methods for non-invasive implant rupture detection are described herein. Such implant rupture detection systems may be used to detect a discontinuity in a casing or shell of an implantable device. Some variations of an implant rupture detection device may comprise a single optical waveguide, such as a silicone optical fiber, embedded in the shell of the implantable device where one end of the optical waveguide may be connected to a photo emitter and the other end of the waveguide may be connected to a photo detector. An optical signal successfully transmitted from the photo emitter through an intact optical waveguide to the photo detector may indicate that the implant shell is intact. An optical signal that is transmitted by the photo emitter but not detected by the photo detector may indicate that there is a discontinuity or rupture in the shell.

One variation of a rupture detection system may comprise a photo emitter, a photo detector, and a single optical waveguide between the photo emitter and the photo detector. The photo emitter may be configured to emit an optical signal through the optical waveguide, and the photo detector may be configured to provide an indication of the receipt of the optical signal to detect a discontinuity in the optical waveguide. Some variations of rupture detection systems may additionally comprise a RFID circuit in communication with the photo emitter and the photo detector. The RFID circuit may be configured to issue commands to the photo emitter, and may be configured to wirelessly transmit the indication from the photo detector to a RFID reader. In some variations, the photo emitter, photo detector, optical fiber, and RFID circuit may be attached to a shell of a breast implant. The optical waveguide may be may be made of a material with similar mechanical properties as the shell of the breast implant, such that the waveguide will break when the shell ruptures. In some variations, the optical waveguide may be a silicone-based optical fiber. In other variations, the optical waveguide may be configured to break when the shell is subjected to mechanical stresses that may eventually lead to shell rupture. The single optical fiber may be distributed across the shell, and may be distributed such that it does not cross itself more than twice. Optionally, the single optical fiber may be distributed across the shell in two or more separate layers of the shell. Rupture detections systems may also comprise a noise reduction sub-circuit. Some variations of noise reduction circuits may be configured to reduce noise and bias that may originate in the photo detector. In some variations, the photo detector may have a dark current, and the noise reduction sub-circuit may reduce a bias in the photo detector by compensating for the dark current. The noise reduction sub-circuit may also be configured to reduce noise that may originate in the single optical waveguide.

Another variation of a rupture detection system that may be used to detect a discontinuity in a shell may comprise a microcontroller, a photo emitter in communication with the microcontroller, a photo detector in communication with the microcontroller, a single optical fiber embedded in the shell, and a RFID circuit in communication with the microcontroller. The RFID circuit may be configured to communicate wirelessly with a RFID reader. A first end of the single optical fiber may be coupled to the photo emitter and a second end of the optical fiber may be coupled to the photo detector. The optical fiber may be made of a material with similar mechanical properties as the shell, such that the optical fiber will break when the shell ruptures. The optical fiber may be made of a silicone-based material. In some variations, the single optical fiber may be distributed across the shell such that it does not cross itself more than twice. The RFID circuit may be configured to be powered by the RFID reader.

One variation of a method for detecting a discontinuity in a breast implant shell may comprise holding a RFID reader close to a breast implant comprising a detection system, where the detection system comprises a photo emitter, a photo detector, and a single optical waveguide therebetween, sending a signal from the RFID reader to the detection system to emit an optical signal from the photo emitter to the single optical waveguide, and interrogating the detection system with the RFID reader to query the photo detector to detect a discontinuity in the optical waveguide based on the reception of the optical signal. In some variations, the discontinuity detection may be performed on a breast implant that may be external to the patient (e.g., before it has been implanted into a patient, or after it has been extracted from the patient), while in other variations, the discontinuity detection may be performed on a breast implant that may be implanted in a patient.

DETAILED DESCRIPTION

Figure 1:
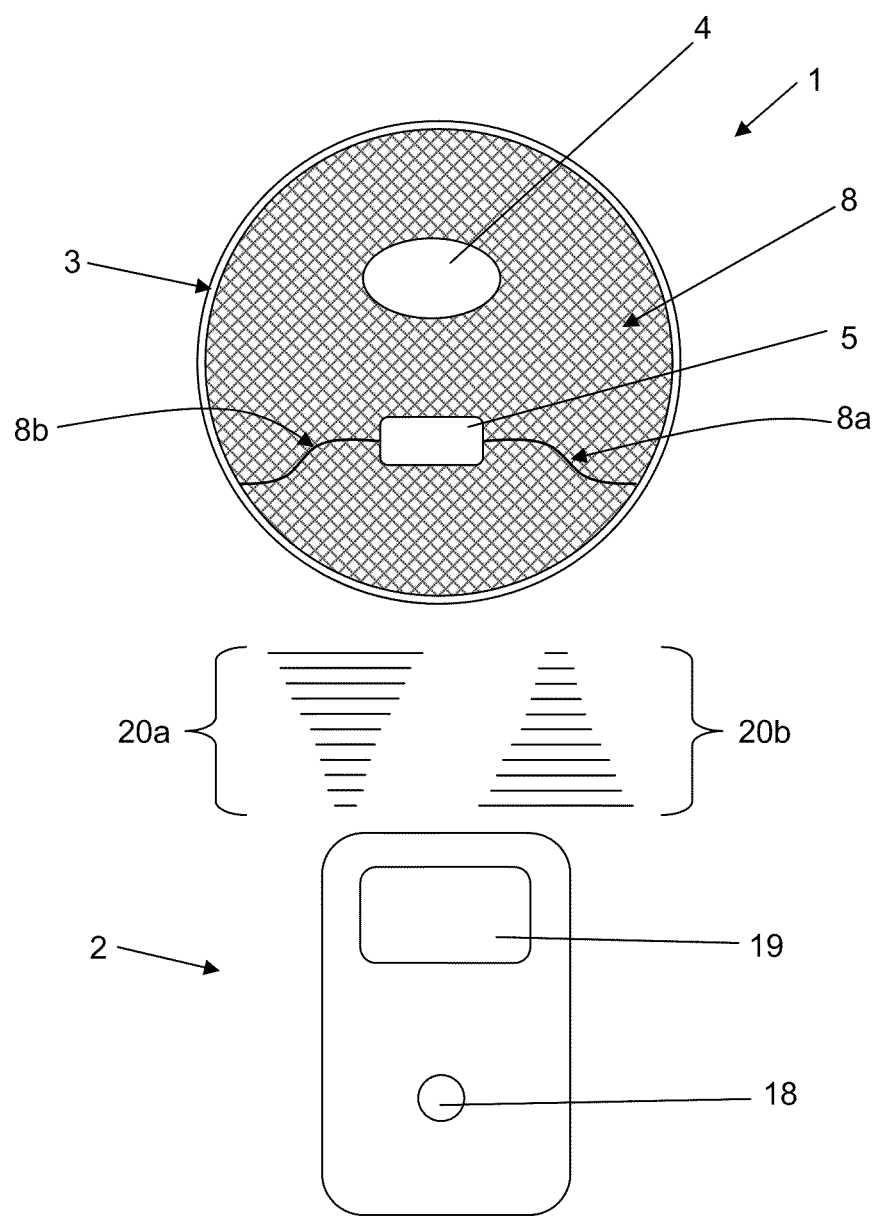
FIG. 1 depicts one variation of a non-invasive rupture detection system for an implantable device.

Devices and methods for non-invasive implant rupture detection are described herein. Such implant rupture detection systems may be used to detect a discontinuity in a casing or shell of an implantable device. The conductivity of a signal through the shell of an implantable device may provide an indication of the condition of the shell. For example, certain implantable devices may comprise a shell with one or more waveguides or silicone fibers embedded and/or encapsulated within the shell. Alternatively or additionally, the one or more waveguides or silicone fibers may be attached to the inner and/or outer surface of the shell (e.g., along or embedded in the inner surface, along or embedded in the outer surface). The one or more silicone fibers may be conductive to measurable physical quantities, such as electrical and/or fluidic and/or mechanical and/or optical quantities. For example, the silicone fibers may be configured to conduct electric currents and/or voltages, or may be configured to conduct mechanical waves or forces along the length of the fiber. Silicone fibers may as be configured as a conduit for liquid and/or gaseous substances, or may be configured as a waveguide for light. A change (e.g., a disruption) in the conductive property of the one or more waveguides or silicone fiber(s) may indicate a change in the integrity of the shell (e.g., rupture, failure, thinning, etc.). Various devices and systems that may be used to detect one or more changes in the conductive property of the one or more silicone fiber(s) associated with the shell of an implant are described herein. As an example, devices and systems for rupture detection of a silicone breast implant by measuring the optical property of a silicone fiber embedded in the implant shell are described, however, it should be understood that similar devices and systems may be used to measure electrical, fluidic, and/or mechanical quantities to detect ruptures or discontinuities in the shell of any implantable device.

Prosthetic breast implants may be constructed with an elastic silicone shell which may be filled with a viscous silicone gel or a sterile saline solution. Decades of debate and healthcare dollars have been spent on how to best ensure the integrity of silicone gel filled prosthetic breast implants, since silicone that has extravasated outside the implant shell may be difficult to extract and can create medical problems. Leaked or extravasated silicone that is not removed may compromise surveillance for cancer detection by either manual exam, mammography, or magnetic resonance imaging studies. However, removal of unnecessary breast parenchyma in an attempt to remove all of the silicone and/or any resultant capsules may result in a permanent deformity to the remaining breast tissue.

Some types of prosthetic breast implants may be filled with high viscosity formulations of silicone gel. A high viscosity silicone filling may flow less freely than a traditional silicone or saline filling, which may make implant rupture detection more difficult. In most cases, the implant failure may be unnoticed by the patient.

Described herein are devices and systems for the non-invasive detection of a rupture or failure in a breast implant. A prosthetic breast implant may comprise a single silicone fiber embedded or encapsulated in or on the surface of the implant shell, where the silicone fiber may be connected to an implant sensor tag. The implant sensor tag may be wirelessly activated from outside the patient's body using an implant tag reader to report the status of the implant shell to a medical practitioner. In some variations, the tensile strength and elasticity of the silicone fibers may approximate the tensile strength and elasticity of the shell. Some variations of prosthetic breast implant rupture detection systems and methods may be configured to non-invasively confirm the integrity of the implant shell to help ensure that a significant proportion of the material is contained within the implant, and is not released into the patient.

A rupture detection mechanism may comprise a single length of a waveguide such as an optical fiber, made from silicone polymer that has been encapsulated and embedded into or on the surface of the elastomeric breast implant shell. The optical fiber is may be distributed across the surface of the implant shell such that it forms a pattern resembling a net that may surround the viscous gel contained within the implant. Both ends of the optical fiber may be connected to a sensor tag attached to the implant, where one end of the fiber may be aligned to accept light from a photo emitter (e.g., a light-emitting diode or laser diode), and the other end of the fiber may be aligned with a photo detector (e.g., a photodiode). In some variations, the implant sensor tag may be encapsulated and/or embedded into the implant shell. The implant sensor tag may contain a passive RFID tag circuit that is powered and controlled by an external implant tag reader comprising a RFID reader circuit. The RFID tag circuit and the other components of the implant sensor tag may be powered by collecting electromagnetic energy provided by the implant tag reader. The RFID tag circuit and the RFID reader circuit may comply with a standard communications protocol such as ISO 15693. The implant tag reader may also contain a visual indicator and/or an audible annunciator to signal the practitioner and/or patient regarding the status of the breast implant shell.

FIG. 1 depicts one example of a breast implant rupture detection system that may be used to non-invasively confirm the integrity of the implant shell. A breast implant (1) may comprise a shell (3), an optical waveguide such as a single optical fiber (8) embedded or encapsulated in the shell (3), and a sensor tag (5) embedded or encapsulated in the shell (3) that may be connected to the first and second ends of the single optical fiber (8). The sensor tag (5) may comprise a photo emitter connected to a first end (8a) of the optical fiber (8), and a photo detector connected to a second end (8b) of the optical fiber (8). The photo emitter may be configured to emit a light signal through the optical fiber, and the photo detector may be configured to detect any light signal that may be transmitted through the optical fiber. The sensor tag (5) may also comprise circuitry configured to transmit and receive electromagnetic signals to and from an external device. For example, the sensor tag (5) may comprise a radio frequency identification (RFID) circuit configured to transmit and receive electromagnetic signals (20a, 20b) to an external RFID tag reader (2). The sensor tag (5) and the RFID tag reader (2) may be in communication with each other, for example, using a wireless protocol that may allow the tag reader (2) to access a set of registers in the sensor tag (5). The RFID circuit of the sensor tag (5) may also be connected to the photo emitter and photo detector, where the RFID circuit may be configured to activate the photo emitter, and receive a response from the photo detector, which may be wirelessly transmitted to the external RFID reader (2).

The RFID reader (2) may comprise circuitry configured to emit an electromagnetic signal (20b) that may be used to provide power to the implant sensor tag (5). The RFID reader (2) may also comprise a display (19) configured to convey the status of the breast implant (1) to a patient and/or practitioner, and a test button (18) configured to control the sensor tag (5) and/or adjust or set functional modes of the RFID tag reader. Alternatively or additionally, the RFID tag reader (2) may comprise other visual, audio, and/or tactile alerts to convey the status of the breast implant (1) to the patient and/or practitioner, such as light-emitting diodes, buzzers, vibratory components, and the like. Various user-initiated or programmed test sequences may be executed upon activation of the test button (18) are described below.

Some variations of a RFID tag reader may be configured to retrieve, format and display data stored in the implanted sensor tag. When called for by the medical practitioner, the RFID tag reader circuitry may emit an electromagnetic signal coded to request data stored in the implant sensor tag. A RFID circuit of the sensor tag may respond by sending return transmission signals containing the requested data. The requested data may be received by the RFID tag reader, and formatted and displayed for the medical practitioner.

Additionally, some variations of a RFID tag reader may comprise a remote display and control device. For example, a RFID tag reader may comprise an additional wireless interface to communicate with another remote display and control device. Some RFID tag readers may use the Bluetooth® protocol to communicate with a cellular telephone such as an iPhone or a laptop computer. Alternatively or additionally, some RFID tag readers may use a WiFi interface to communicate with an internet service. In this way, implant data may be displayed and recorded in conventional computer databases, and/or may be provided to a practitioner at a remote location.

Figure 2:
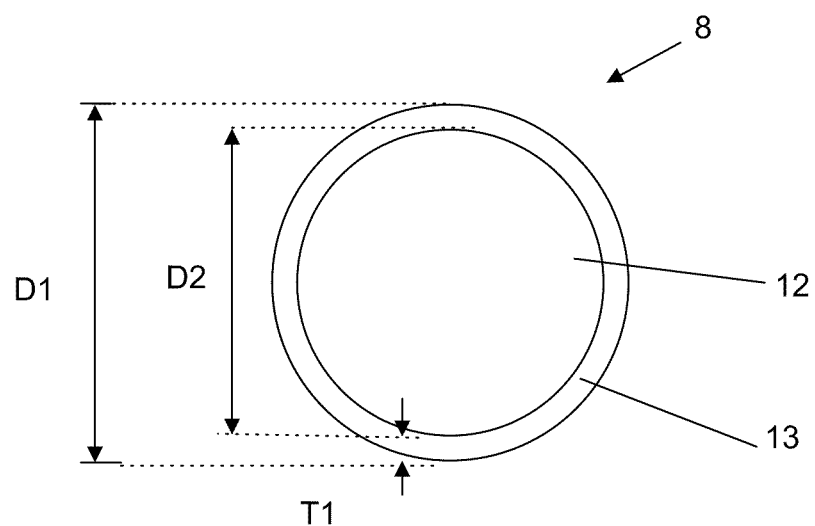
FIG. 2 is a cross-sectional view of one example of a silicone optical fiber that may be used with an implantable device.

FIG. 2 depicts one variation of an optical waveguide that may be included with the shell of a breast implant. The optical fiber (8) may be a coaxial construction of silicone polymer comprising a silicone polymer core (12) surrounded by a silicone cladding layer (13). The optical fiber (8) may have a diameter D1 from about 60 micrometers (microns) to about 1100 microns, e.g., from about 200 microns to about 300 microns. The core (12) may have a diameter D2 from about 50 microns to about 1000 microns. The cladding layer (13) may have a thickness T1 from about 10 microns to about 50 microns. An optical waveguide may have deformation and wear properties that are similar to the deformation and wear properties of the shell of a breast implant. For example, the mechanical properties of the optical fiber (8) may be similar to the mechanical properties of the implant shell (3), which may help to maintain the overall strength of the implant shell and to help ensure that a rupture resulting from flexural fatigue of the shell (3) will cause a similar rupture in the optical fiber (8). Matching or approximating the mechanical properties of the optical fiber and implant shell may also help to avoid tearing of the shell in the vicinity of optical fiber when the breast implant (1) is deformed (e.g., during implantation, routine manipulation, etc.). The tensile strength and elongation of the optical fiber (8) may be adjusted through the formulation of the silicone polymer of the core (12) and the cladding (13) to approximate the tensile strength and elongation of the implant shell (3). In some variations, implant shells may be made from DOW Corning Silastic I and Silastic II, which are polydimethylsiloxane polymers. These materials may have a minimum tensile strength of 900 psi and an elongation of 550%. An optical fiber made from an optically clear, medical grade silicone, such as NuSil MED-6233P, may have a minimum tensile strength of 750 psi and an elongation of 305%. Selecting chemically similar materials for the shell and the fiber (e.g., selecting a silicone fiber for a silicone shell) may also help improve the adhesion between the shell and the fiber. Furthermore, since the properties of silicone polymers are well understood, using a silicone optical fiber may not introduce new issues of patient safety in the event of a rupture where the optical fiber may come into contact with biological tissue and/or fluids of the patient. This may help to reduce the biocompatibility testing that may be required to achieve regulatory compliance.

In some variations, an optical fiber embedded or encapsulated in a shell may be configured to anticipate a rupture of the shell. For example, an optical fiber may be configured to break before the shell ruptures (e.g., the optical fiber may have mechanical properties such that the optical fiber ruptures before the shell ruptures). In some variations, the polymers comprising an optical fiber may be selected with flexural and fatigue properties that that differ from the shell such that the continuous optical waveguide may be broken when the shell (3) is subjected to mechanical stresses that may increase the risk of shell rupture and/or eventually result in its rupture. Alternatively or additionally, an optical waveguide may have certain characteristics that may be predictive of an impending shell rupture, and/or may indicate an increased risk of shell rupture. Some variations of a rupture detection system may measure such characteristics of the optical waveguide, and may provide this information when queried by a practitioner and/or patient. For example, a change in the optical loss associated with the waveguide may indicate an impending rupture (e.g., the optical loss associated with the waveguide may increase as a result of mechanical stresses applied to the shell (3) that may eventually result in its rupture). In some variations, pressure applied to the shell may increase the optical loss associated with a waveguide embedded or encapsulated in the shell, which may signal a condition that may result in an increased risk of shell rupture.

In some additional variations, the optical fiber may be made from a material with a lower hardness and tensile strength than the implant shell, and may be distributed across and bonded to the inner surface of implant shell without being embedded or encapsulated into it. The adhesion between the optical fiber and the inner surface of the implant shell may be sufficiently high to help ensure that a rupture in the implant shell will result in a simultaneous break in the optical fiber. The sensor tag may also be bonded to the inner surface of the implant shell rather than embedded or encapsulated into it. This may allow the implant shell to be fabricated without discontinuities that may contribute to reducing its resistance to flexural fatigue failures. In this variation, the optical fiber may not contribute significantly to the containment strength of the implant shell.

The core (12) and cladding layer (13) may each have an index of refraction as appropriate for the use of the optical fiber (8) as a multi-mode optical waveguide. For example, the core (12) may have an index of refraction that may be about 0.01 to 0.03 higher than the index of refraction of the cladding layer (13). For example, the silicone core (12) may have an index of refraction from about 1.4 to about 1.6, e.g., about 1.43, while the silicone cladding layer (13) may have an index of refraction about 1.41. The difference between the index of refraction of the core (12) and cladding layer (13) may determine the acceptance angle of the optical fiber (8), where the acceptance angle may be the maximum angle measured from the axis of the optical fiber at which light will enter and propagate through it. In some variations, the diameter D1 of the optical fiber (8), the index of refraction for the core (12) and the cladding (13) may be selected to achieve an acceptance angle that is consistent with the alignment tolerance between the optical fiber (8) and a photo emitter of the sensor tag (5). In some variations, the core (12) and the cladding (13) may be selected to transmit photons with a wavelength in the range of about 800 nanometers (nm) to about 1000 nm. For example, dimethyl silicone polymer compositions may transmit photons with a wavelength of 1310 nm with losses of about 0.14 dB/cm, or photons with a wavelength of 850 nm with losses of less than about 0.01 dB/cm, or photons with a wavelength of 400 nm with losses of about 0.03 dB/cm. The optical fiber (8) may also be constructed of various core and cladding materials to help reduce optical loss. For example, the optical fiber (8) may be made of a transmissive, dimthylsilicone polymer, which may have an optical loss of approximately 0.01 dB/cm.

In some variations, a bare core of an optical fiber m made without a cladding layer, thereby simplifying its manufacture. The optical waveguide is formed when the bare core is completely encapsulated and surrounded by the implant shell material which has an appropriate index of refraction. The index of refraction of the bare core may be greater than the index of refraction of the shell in which the fiber is embedded. For example, the index of refraction of the bare core of a silicone optical fiber may be about 1.43, and the silicone implant shell may have an index of refraction of about 1.41. Selecting an implant shell made of a material with a lower index of refraction than the bare core of an optical fiber and completely surrounding the bare core with the implant shell may help to ensure that there is only one optical pathway through the shell (i.e., through the optical fiber). This may reduce the possibility that light bypasses a shell rupture if the optical fiber is distributed such that it crosses over itself (which may occur if the optical fiber is in direct contact with another section of the fiber at a cross over point).

Figure 3:
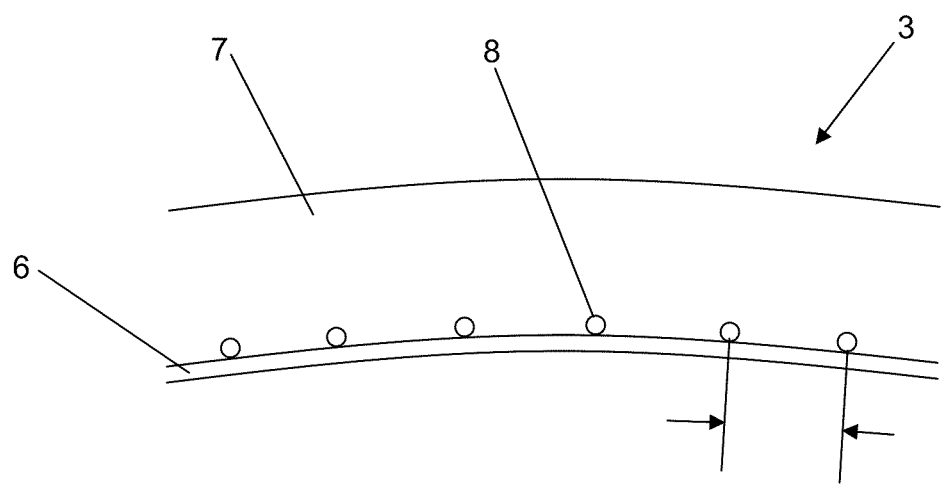
FIG. 3 is a cross-sectional view of a portion of an implant shell.

The optical fiber (8) may be distributed across the implant shell (3) in two dimensions such that the spacing between segments of the optical fiber (8) may be selected according to the size of the rupture to be detected. For example, to detect shell ruptures that are 2 mm or larger, the spacing between the optical fiber segments may be less than or equal to 2 mm. In some cases, a 200 cc prosthetic breast implant may use approximately 32 meters of optical fiber that is spaced at 2 mm intervals. Spacing intervals between segments of the optical fiber (8) may be less than 2 mm to detect ruptures of a smaller size, e.g., spacing intervals may be less than or equal to 1 mm, 0.5 mm, 0.25 mm, 0.1 mm to detect pinhole failures or ruptures greater than or equal to 1 mm, 0.5 mm, 0.25 mm, 0.1 mm, respectively. FIG. 3 depicts a cross-section of the implant shell (3) with the optical fiber (8) distributed across the shell (3) with a spacing interval D3, where D3 may be less than about 2 mm (e.g., 1.5 mm, 1.0 mm, 0.25 mm). The optical fiber (8) may be distributed across the surface of a first shell layer (6), and embedded in a second shell layer (7). Additional shell layers may be applied over the second shell layer (7) as appropriate. For example, the thickness of each layer may be related to the overall diameter of the optical fiber (8), and may range from about 200 microns to about 400 microns. In some variations, the interval spacing of the optical fiber may be uniform across the implant shell, while in other variations, the interval spacing of the optical fiber may be non-uniform across the shell. For example, the interval spacing may be decreased around regions of the shell that may be particularly prone to rupture or failure, such as around tightly curved or frequently manipulated regions, and the spacing may be increased around flatter or less manipulated regions of the implant shell. The optical fiber (8) may be distributed across a substantial portion of the shell, for example, it may be distributed across about 50% to about 100% of the area of the shell (e.g., 55%, 60%, 75%, 85%, 95%, 100%). In some variations, the optical fiber may be distributed across substantially 100% of the area of the shell which may help to detect a rupture located at any point on the shell. In other variations, the optical fiber may be distributed across less than about 50% to about 100% of the shell, e.g., from about 10% to about 50%.

Figure 4:
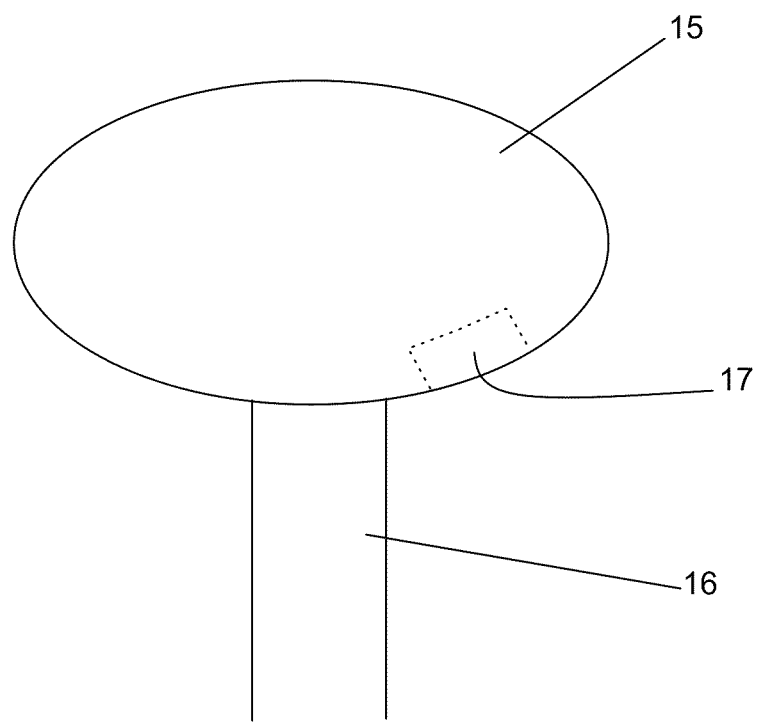
FIG. 4 depicts one example of a mandrel and mandrel head that may be used to manufacture an implant shell.

Some methods of manufacturing a silicone implant shell with a waveguide distributed across it may use a mandrel device that is depicted in FIG. 4. The implant shell may be formed in layers by dipping the head (15) of a mandrel (16) into liquid silicone polymers followed by curing (e.g., by the application of heat). The optical fiber (8) may be embedded in the implant shell (3) by distributing the fiber across the first shell layer (6), and then applying additional shell layers (e.g., the second shell layer (7)) over the optical fiber, which may encapsulate the optical fiber within the shell. The implant sensor tag (5) may be similarly encapsulated in the implant shell (3). During the manufacture of the implant shell (3), the ends of optical fiber (8) may be bonded to the implant sensor tag (5), and the implant shell tag (5) may be placed into a mandrel recess (17). Subsequent layers of the silicone implant shell may be applied over the optical fiber (8) and sensor tag (5), and may envelop and encapsulate the implant sensor tag and the optical fiber. When a desired thickness of implant shell (3) has been formed and cured, the implant shell (3), including the implant sensor tag (5), may be removed from the mandrel head (15) by stretching a fill hole (4) of the implant over the mandrel head (15). Encapsulation of the optical fiber (8) within the implant shell (3) may help protect the small diameter optical fiber (8) during the remainder of the manufacturing and product packaging processes. In some variations, the implant sensor tag may be placed over the mandrel recess or patch site after the implant is filled.

Another example of a manufacturing process for the implant shell (3) may use an additional set or sets of the optical fiber, photo emitter and photo detector. The optical fiber may be distributed across a portion of the implant or in a particular orientation, and the ends of the optical fiber may be attached to the sensor tag in one step. In a subsequent step, an additional optical fiber may be distributed across the surface to complete the coverage of the implant. This approach may have the additional effect of eliminating the difficult task of splicing two pieces of silicone optical fiber (8) into a single continuous path.

One example of a manufacturing process that may help ensure that a waveguide such as an optical fiber (e.g., optical fibers with or without a cladding layer) is surrounded entirely by the shell material may comprise initially coating the mandrel head (15) with a first silicone layer, and distributing the optical fiber over the mandrel head (15) with a pattern that does not cross over itself. Next, the mandrel head may be dipped in liquid silicone to form a second layer covering the optical fiber, and the second layer may be cured. Next, the remainder of the optical fiber may be distributed across the mandrel head (15), over the second layer, in another direction such that the optical fiber may cross over the portion of the fiber embedded between the first and second layers. A third silicone layer may be applied over the second layer to complete the encapsulation of the optical fiber in the implant shell. This manufacturing process may help ensure that a silicone layer with the appropriate index of refraction separates the optical fiber at all points and may permit the use of an optical fiber without a cladding layer to be used as a waveguide.

Flaws, contamination, or the inherent characteristics of the material(s) of an optical fiber may sometimes diffuse a small fraction of light directed along its length such that a portion of the light is no longer contained within the optical fiber. In some variations, the layers of optical fiber within an implant shell may be separated with a material opaque or absorptive to light with wavelengths that may otherwise elicit a response from a photo detector. Alternatively or additionally, the optical fiber itself may be coated with a material opaque or absorptive to light with wavelengths that may elicit a response from a photo detector. The layers of opaque materials may act to absorb any diffused light from the optical fiber so that the light is not coupled back into segments of optical fiber at cross over points, which may otherwise allow light to bypass a break in optical fiber. The layer of opaque material may additionally eliminate the effect of ambient light. Examples of opaque formulations of silicone polymers may include pigments or colorants such as 61-86250 (IR Black) from Ferro Corporation, which is opaque to infra-red light with wavelengths of about 800 nm to 960 nm.

Optionally, the exterior surface of an implant shell may be coated with a material that is opaque or absorptive to light with wavelengths that may otherwise elicit a response from a photo detector. This coating may help to reduce the effect of ambient light on the implant. It may be desirable to confirm the proper operation of the rupture detection system prior to implantation, for example, to determine the rupture status of the implant before it is implanted. The opaque coating may help to block ambient light from reaching the photo detector that may cause a false indication that the implant shell has not been ruptured. Examples of opaque formulations of silicone polymers may include pigments or colorants such as 61-86250 (IR Black) from Ferro Corporation, which is opaque to infra-red light with wavelengths of about 800 nm to 960 nm.

Optionally, a surface finish or texture may be applied to an implant shell. For example, the mandrel head (15) may be made with a mold negative of the surface finish or texture desired for the outer surface of the implant shell. After completely forming the implant shell, it may be removed from mandrel head (15) with the surface finish or texture on the inside. The implant shell may be turned inside out so that the surface finish or texture is now on its outside surface. The implant shell may then be filled and completed using conventional techniques.

While the overall shape of the silicone shell has been depicted as ellipsoidal, spherical, etc., it should be understood that the silicone shell may have any suitable geometry. For example, the silicone shell may resemble a teardrop with an elliptical portion that is elongated and tapered along one side, or may have an irregular geometry tailored to the anatomical region where the device is to be implanted. In some variations, the silicone shell may have an anatomically designed geometry, teardrop or other configuration whereby an upper portion of the implant has less projection or fill than an inferior portion of the implant.

As described above, the optical fiber may be distributed across the shell with a spacing interval in accordance with the size of the rupture to be detected. The optical fiber may also be distributed across the shell to reduce the optical attenuation of light passing through the fiber. For example, the optical fiber (8) may be distributed across the shell with a radius of curvature greater than about 10 times to about 20 times its diameter D1 to help reduce any intensity attenuation of the light passing through the fiber (8). Optical fiber distribution patterns may be selected such that the optical fiber is not curved or bent with a radius of curvature that may result in optical attenuation effects. While the fiber distribution patterns described below are applied across breast implant shells that may be generally circular or round, it should be understood that similar patterns may be applied across shells with a non-uniform geometry.

Figure 5A:
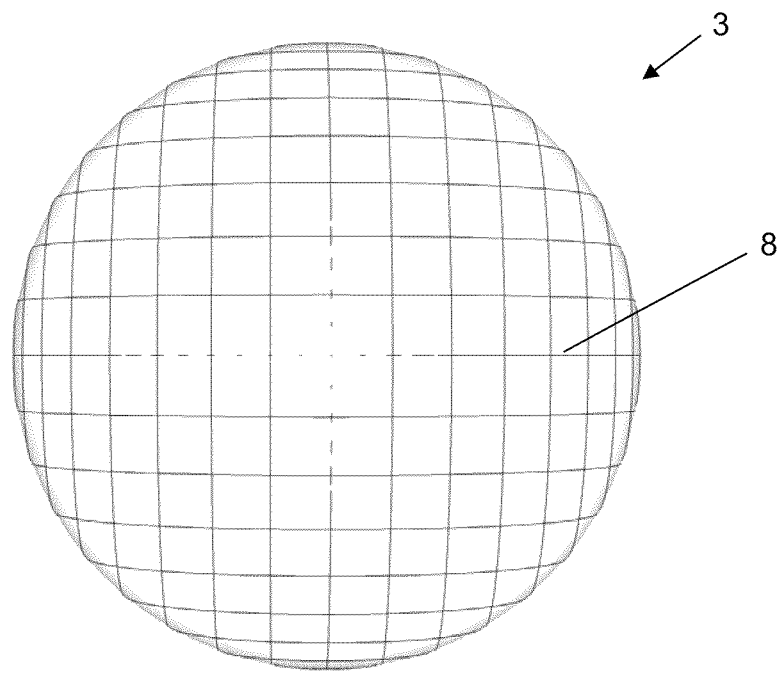
FIG. 5A is a top view of one variation of an optical waveguide distribution pattern for an implant shell.
Figure 5B:
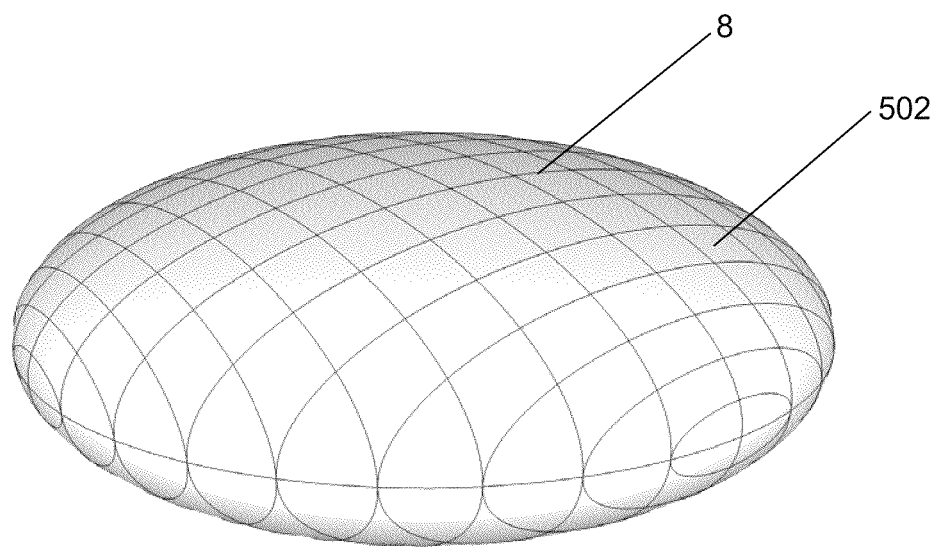
FIG. 5B is an isometric view of the optical waveguide distribution pattern of FIG. 5A.

One example of an optical fiber distribution pattern is depicted in FIGS. 5A-5E. FIG. 5A is a top view of the implant shell (3), showing the regular spacing of the optical fiber (8) in two dimensions. FIG. 5B is an isometric view of the implant shell (3), where the fiber (8) may uniformly cover and partition the shell (3) into various regions (502) bounded by the fiber. The regions (502) may have similar areas, lengths, and widths, though the geometry of various regions (502) may not be identical. The thickness of the implant shell (3) containing the embedded optical fiber (8) may be determined in part by the number of times the optical fiber crosses over itself. In the example of the distribution pattern depicted in FIGS. 5A and 5B, the optical fiber (8) crosses over itself at many points across the surface of the implant shell (3), but there may be no points on the shell where more than two segments of the optical fiber (8) cross over one another. In other examples, a distribution pattern may be used where more than two segments of the optical fiber cross over.

Figure 5C:
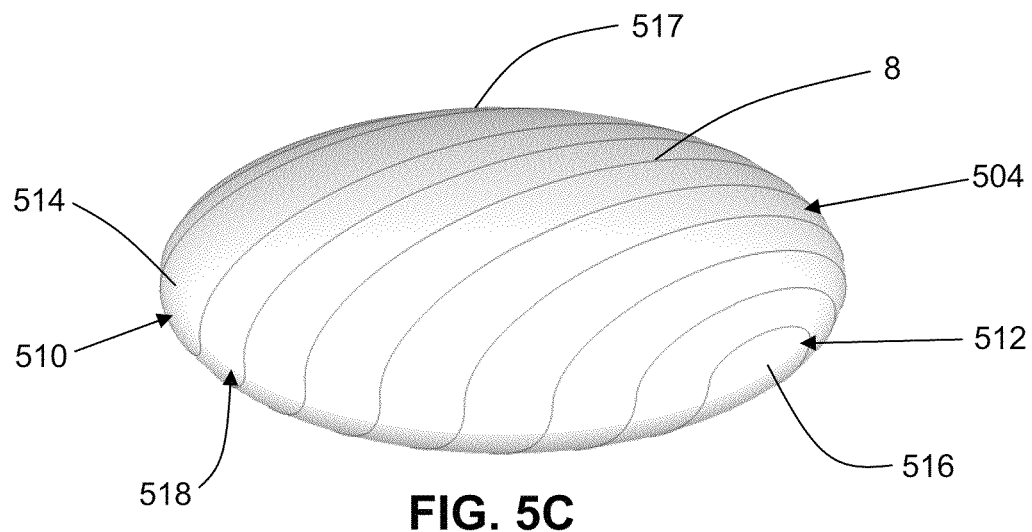
FIGS. 5C-5E depict different layers of the optical waveguide distribution pattern of FIG. 5A.

The crossing of a first segment of the optical fiber over a second segment of the optical fiber may occur over multiple layers of the shell (i.e., the first and second intersecting segments are separated by a layer of shell material in between), or may cross over each other in the same layer of the shell. For example, the distribution of the optical fiber across the implant shell as depicted in FIGS. 5A and 5B may result from overlaying the fiber distribution pattern of a first inner layer (504), a second layer (506), and a third outer layer (508), where each layer may be a layer of the shell, or may be layers of the optical fiber distributed across a single layer of the shell. An optical fiber that is distributed such that it crosses itself in a single layer of the shell may have an opaque cladding layer, or may have an opaque coating, which may help reduce any optical cross-talk, bypass or interaction between overlapping fiber segments. FIG. 5C depicts the optical fiber distribution across the first layer (504) of the implant shell, where the optical fiber (8) may be distributed across the three-dimensional surface of the implant shell (3) with curved regions that may be similar to the interlocking shapes bounded by the semicircular arc segments of the seam on a baseball. The curved regions on the surface of the first layer (504) may be shaped identically, but flipped to the opposite side and are rotated ninety degrees with respect to each other. For example, a first curved region (510) located on top portion (514) of the first layer (504) and a second curved region (512) located on a bottom portion (516) of the first layer (504) may have identical shapes, but the top portion (514) may be positioned orthogonally with respect to the bottom portion (516). The curved regions may be bounded by loops of optical fiber (8) which may be distributed across the broadly domed top surface (517), and may change orientation as it curves back around one side of the shell and curves back across the top surface to the opposite side of the shell. Each loop of optical fiber (8) on the layer may be placed adjacent to the previous loop such that they do not cross. For example, the bend radius may be reduced in one orientation and increased in the other (e.g., the bend radius of a third semicircular region (518) may be greater than that of the first semicircular region (510)). Such a looping pattern may be continued until a minimum bend radius is reached in one orientation (e.g., such that the radius of curvature at any point along the optical fiber does not cause significant reductions in the light transmission properties through the optical fiber (8)).

Figure 5D:
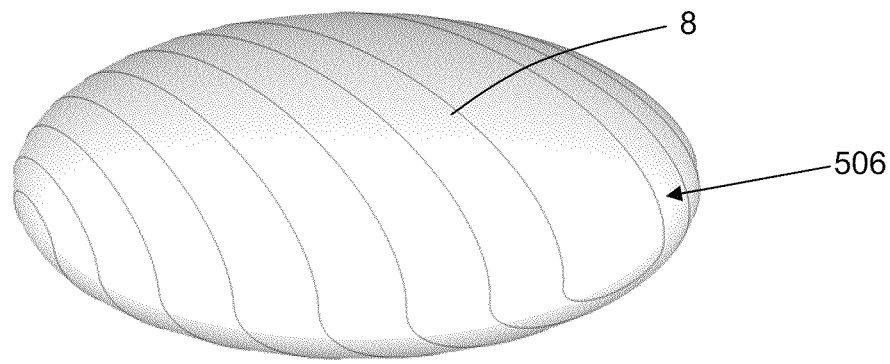
Figure 5E:
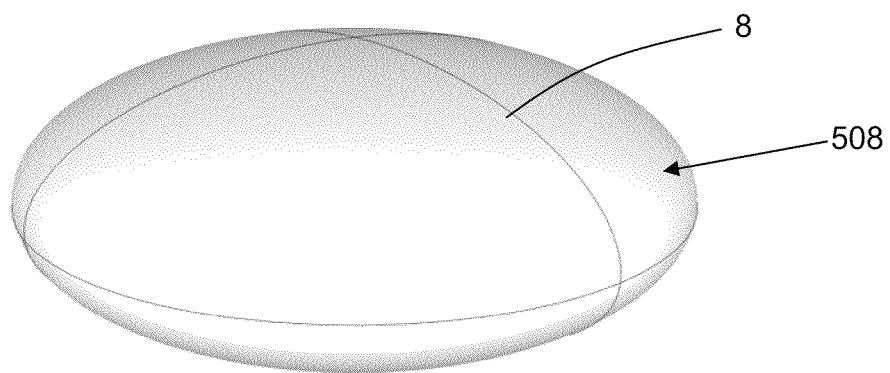

FIG. 5D depicts the optical fiber distribution of the second layer (506) of the implant shell, where the optical fiber (8) may be distributed similarly to the pattern in the first layer (504), but rotated by a quarter turn about the axis of the implant shell (3). The distribution of the optical fiber (8) in the third layer (508) is depicted in FIG. 5E, where optical fiber (8) may be placed around the girth of the implant shell in two orientations and around the circumference of implant. One or more loops may be placed adjacent to the loops on the third layer (508) to fill in any regions in the implant shell where the minimum bend radius limits fiber spacing at the center. Loops on the third layer (508) around the circumference of the implant shell (3) may be offset slightly to ensure that only two segments of optical fiber (8) cross over one another.

Figure 6A:
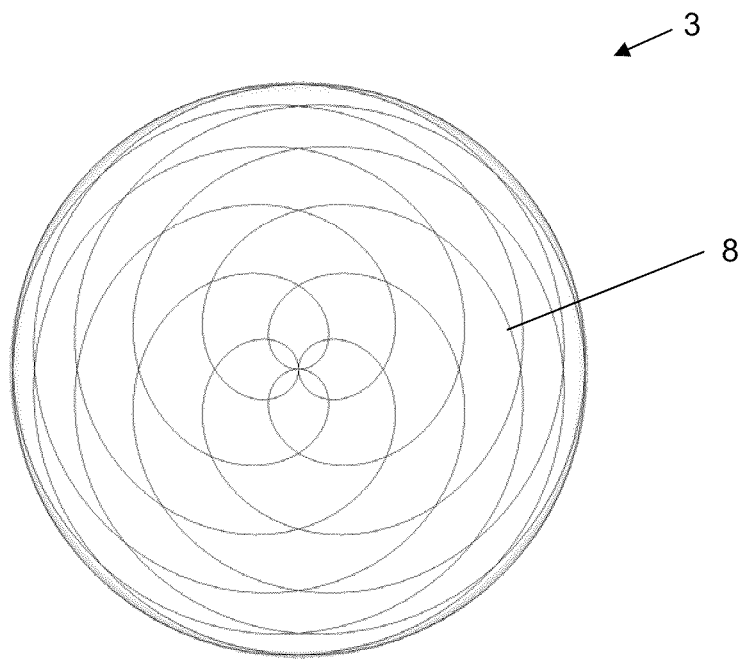
FIG. 6A is a top view of another variation of an optical waveguide distribution pattern for an implant shell.
Figure 6B:
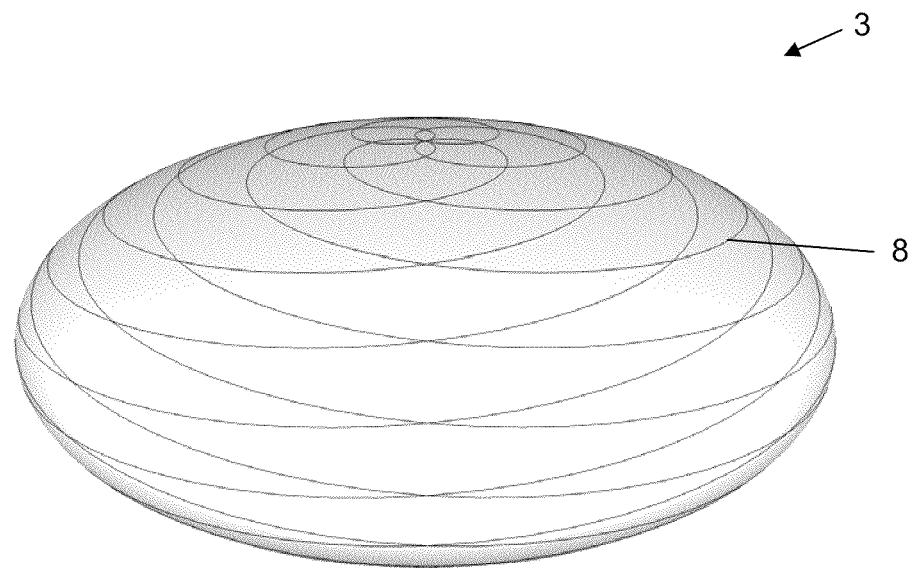
FIG. 6B is an isometric view of the optical waveguide distribution pattern of FIG. 6A.
Figure 6C:
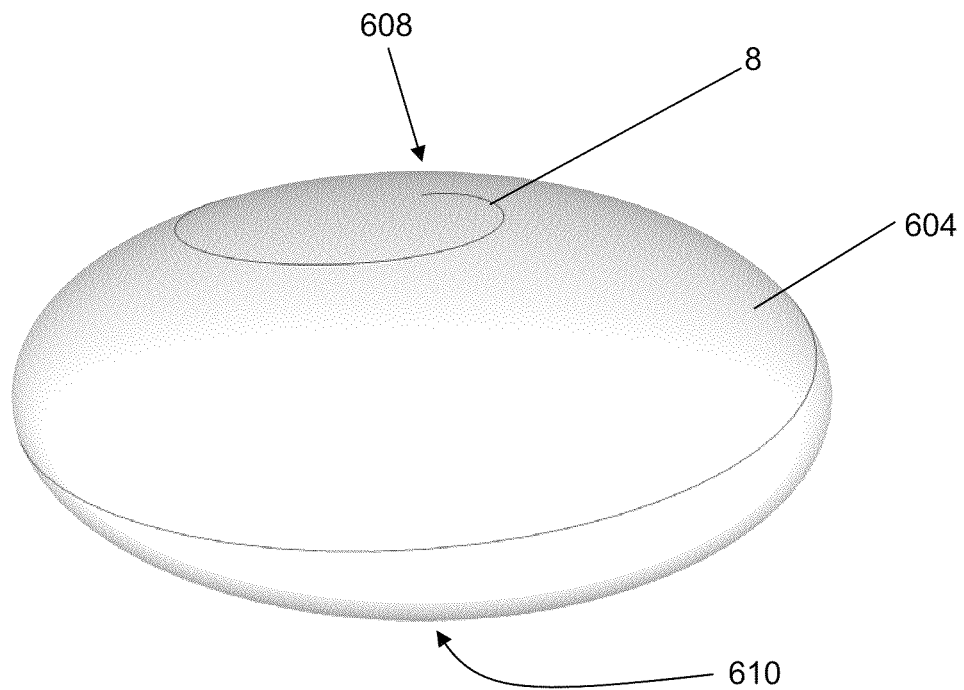
FIGS. 6C and 6D depicts different layers of the optical waveguide distribution pattern of FIG. 6A.
Figure 6D:
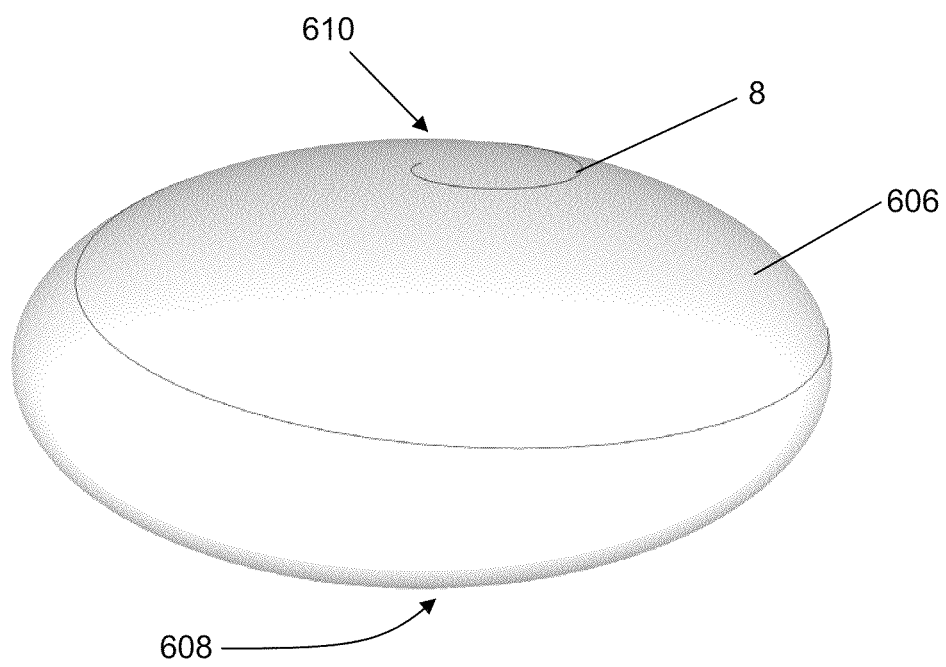

Another example of an optical fiber distribution pattern is depicted in FIGS. 6A-6D. FIG. 6A is a top view of the implant shell (3), showing the spacing of the optical fiber (8) in two dimensions. FIG. 6B is an isometric view of the implant shell (3), where the fiber (8) may uniformly cover and partition the shell (3). The optical fiber (8) may be distributed across the implant shell (3) using one or more three-dimensional spirals. The optical fiber (8) may be distributed across two or more layers of the implant shell (3), or in a single layer of the shell. For example, the fiber distribution pattern across the implant shell (3) as depicted in FIGS. 6A and 6B may be obtained from overlaying the fiber distribution pattern of a first inner layer (604) of the implant shell and a second outer layer (606). FIG. 6C depicts the curvature of the optical fiber (8) as it spirals around the first layer (604) of the implant shell, originating at a first portion (608) of the shell. The spiral of the optical fiber (8) may reverse direction and enter the second layer (606) at a second portion (610) of the implant shell, where the second portion (610) may be opposite the first portion (608), as depicted in FIG. 6D. Such fiber distribution patterns may be shifted and repeated to produce the pattern depicted in FIGS. 6A and 6B.

In some variations, a plurality of waveguides or optical fibers may be distributed across the shell. The plurality of optical fibers may be distributed in patterns similar to those described above, or may be distributed in alternative patterns. In some variations, each of the plurality of optical fibers may be distributed across one layer of the shell, such that no two optical fibers may occupy the same shell layer. For example, a first optical fiber may be distributed across a first layer of the shell, and a second optical fiber may be distributed across a second layer of the shell, where the first and second optical fibers may cross over each other in separate layers. Alternatively or additionally, a plurality of waveguides or optical fibers may be distributed across a shell such that each optical fiber occupies a partition of the shell and does not overlap with an optical fiber that occupies another partition of the shell. For example, a first optical fiber may be distributed across a first region of a layer of the shell, and a second optical fiber may be distributed across a second region of the layer of the shell, where the first region and the second region do not overlap with each other, e.g., the first optical fiber may be distributed across a first half of the surface of the shell while the second optical fiber may be distributed across a second half of the surface of the shell.

Figure 7:
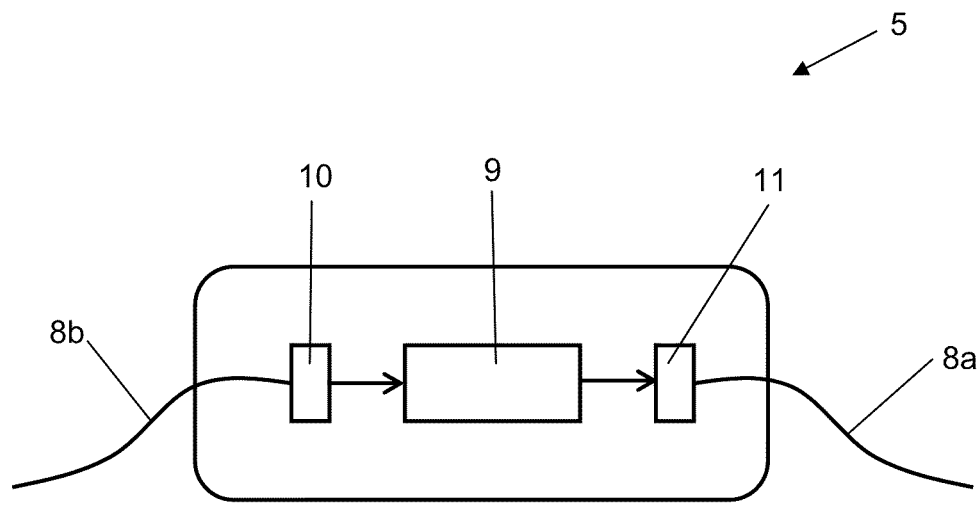
FIG. 7 is a block diagram of one variation of a sensor tag that may be included with an implantable device.

The sensor tag (5) may be within, embedded in, encapsulated in, or attached to an inner or outer or internal portion of the shell (3). The sensor tag may be embedded in, encapsulated in, or attached to a posterior portion of the shell (i.e., the portion of the shell that positioned against the chest wall of a patient after implantation) or an anterior portion of the shell. One variation of the sensor tag (5) is depicted in FIG. 7. The sensor tag (5) may have any geometry suitable for the attaching to the implantable device. For example, the sensor tag may be shaped as a rectangle, square, circle, oval, ellipse, etc., and/or may have a profile that follows the contours and curves of the implantable device. The first end (8a) of the optical fiber (8) may be aligned with, and/or attached to, and/or in the proximity of, a photo emitter (11) of the sensor tag (5). The second end (8b) of the optical fiber (8) may be aligned with, and/or attached to, and/or in the proximity of a photo detector (10) of the sensor tag (5). In some variations, the first and second ends (8a, 8b) may be attached to the photo emitter or detector using an optically clear adhesive, such as Master Bond UV10FL-1 or the like. An opaque coating may be applied over the adhesive to block any stray light from entering the optical fiber (8), e.g., any stray light that may activate the photo detector (10). The photo emitter (11) and the photo detector (10) may be oriented such that light emitted from the photo emitter (11) cannot be conveyed to the photo detector (10) without going through the optical fiber (8). The sensor tag (5) may also comprise sensor tag circuitry (9) to control the photo emitter and detector, which may be configured to communicate wirelessly with an external RFID reader. In some variations, the sensor tag circuitry (9) may be located between the photo emitter (11) and the photo detector (10).

In some variations, the sensor tag may be configured to store and record data associated with the breast implant and this data may be available for display upon its transfer to the implant tag reader. Implant data, for example, such as the manufacturer, model, style, type, size, date of manufacture, lot number, and serial number, as well as surgical implantation data such as the implantation date, location or facility and surgeon may be stored along with a log of when the implant rupture status has been checked. Optionally, commands and status communications between the RFID tag reader and the implant sensor tag may be secured with passwords or may be encrypted such that data stored in the implant sensor tag is not subject to inadvertent access or tampering.

Figure 8:
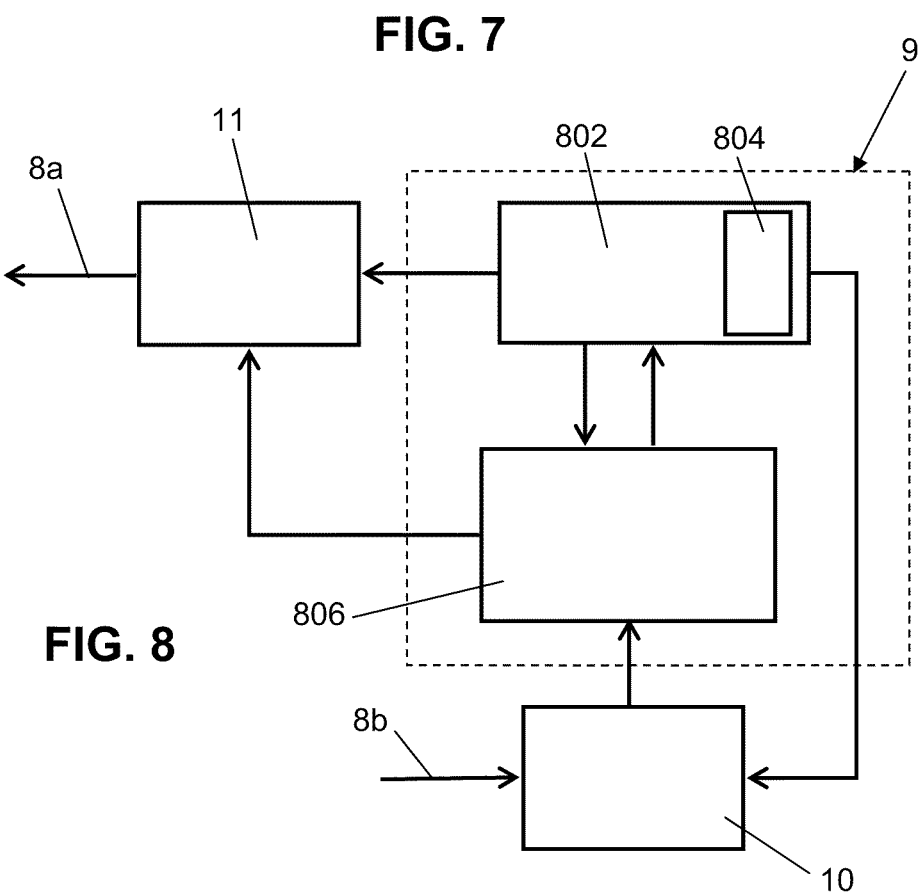
FIG. 8 is a block diagram of one example of sensor tag circuitry that may be included with an implantable device.

FIG. 8 depicts one example of sensor tag circuitry that may be used in an implantable device for non-invasive rupture detection. The sensor tag circuitry (9) may comprise a RFID circuit (802) comprising an antenna (804), a microcontroller (806) in communication with the RFID circuit (802), photo emitter (11), and photo detector (10). The RFID circuit (802) and the antenna (804) may be configured to transmit and receive electromagnetic energy through varying thicknesses of biological tissue (such as breast parenchyma that may range in thickness from about 1 cm to about 10 cm). The antenna (804) may be located adjacent to or in proximity of the RFID circuit (802), or may be located apart from the RFID circuit (802). For example, the RFID circuit may be located on a posterior portion of the implant while the antenna may be located on an anterior portion of the implant. The RFID circuit (802) and the antenna (804) may be configured to receive electromagnetic energy that may be used to provide power to the sensor tag circuitry (9), as well as to the photo emitter, photo detector, microcontroller, and any other electrical components in the sensor tag (5). The RFID circuit (802) may also be configured to receive and transmit wireless signals to communicate with other devices, such as the RFID tag reader (2). For example, RFID circuit (802) may be configured to receive a signal from the RFID tag reader (2) that activates the microcontroller and/or photo emitter and/or detector to initiate a test sequence to determine the status of the implant shell. The RFID circuit (802) may also be configured to wirelessly transmit data related to the status of the implant shell to the RFID tag reader (2) at the conclusion of the test sequence. In some variations, the RFID circuit may also comprise a set of readable and/or writable registers that may be configured to store executable test programs and any associated data. The photo emitter (11) may be a light-emitting diode or a laser diode, and the photo detector (10) may be a photo diode. Photo emitters and detectors may be selected such that the sensor tag is able to detect ruptures in an implant shell despite any optical loss that may occur along the fiber (e.g., 32 dB of optical loss over an optical fiber with a length of 32 meters). Different variations of sensor tag circuitry and test sequences are described below.

Figure 9:
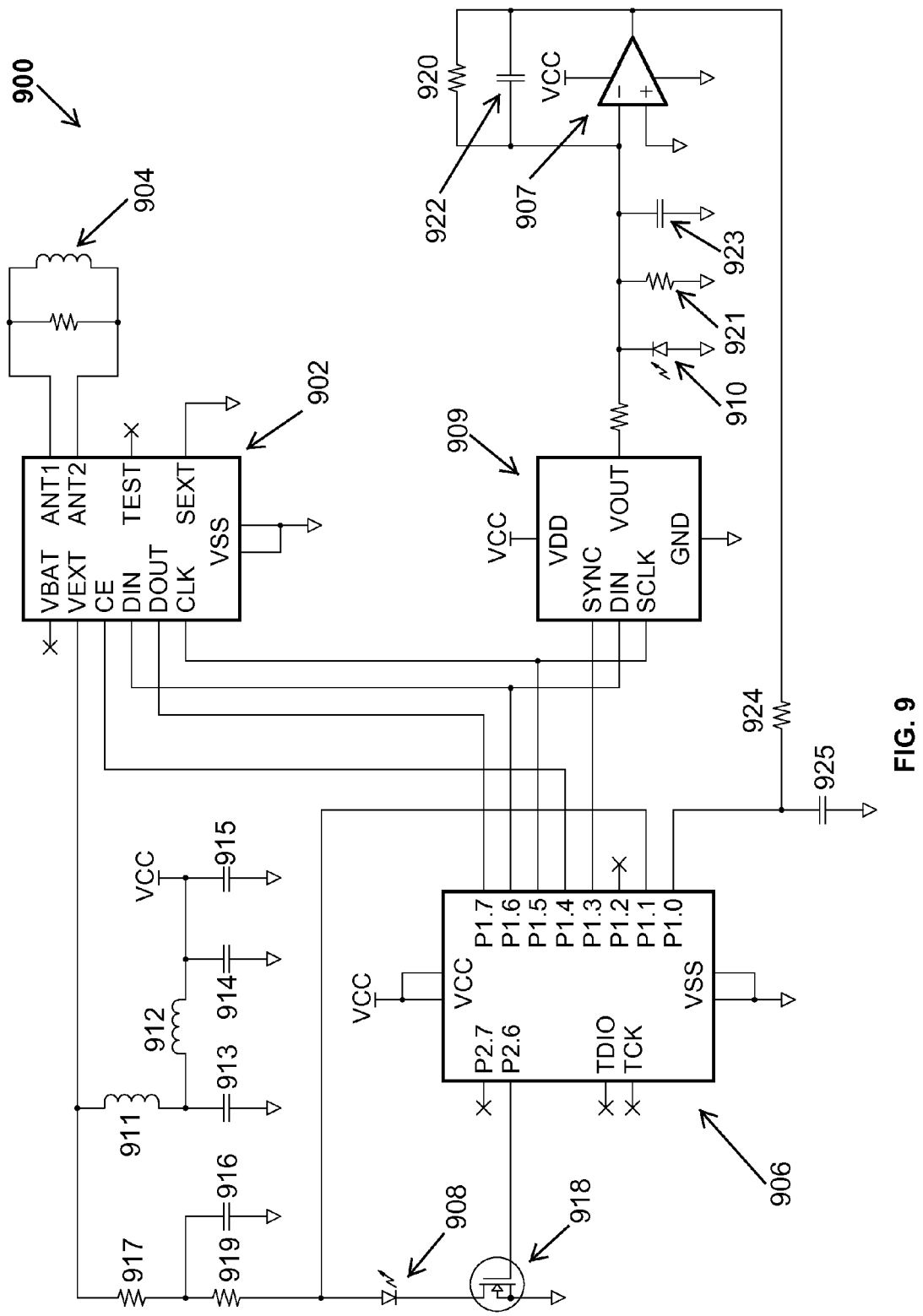
FIG. 9 is schematic diagram of one variation of a sensor tag that may be included with an implantable device.

FIG. 9 depicts a schematic diagram for one example of an implant sensor tag. Sensor tag (900) may comprise a RFID tag circuit (902) and an antenna (904) connected to the RFID tag circuit. The RFID tag circuit (902) may comprise an integrated circuit with a serial peripheral interface (SPI) and a VEXT terminal that may be used to power additional devices (e.g., an IDS-Microchip SL13A). The antenna (904) may be a loop antenna that may be used to collect electromagnetic energy, as well as for wireless communications (e.g., radio communications). The loop antenna may have an inductance of about 5.5 micro henries and may be constructed any suitable method, (e.g., using printed circuit board techniques). The loop antenna and a capacitor inside the RFID tag circuit (902) may form a tank circuit tuned to 13.56 MHz. The sensor tag (900) may also comprise a microcontroller (906), a photo emitter (908), and a photo detector (910). The microcontroller (906) may be any appropriate microcontroller chip, such as Texas Instruments MSP430F2002 and the like. The photo emitter (908) may be a laser diode that is configured to emit a narrow beam for efficient coupling to the optical fiber (8) (e.g., a Roithner CHIP-980-P50 laser diode). The photo detector (910) may be a photodiode, such as a Hamamatsu S1336. The RFID tag circuit (902) may supply D.C. power for one or more of the components of the sensor tag (900). For example, the power supplied by the RFID tag circuit (902) to the microcontroller (906), the photo detector (910) and any additional electrical components (e.g., circuitry associated with the photo detector) may be filtered by a low pass LC network (e.g., a low pass LC network comprising 911, 912, 913, 914, 915), and is labeled as VCC. Unfiltered power supplied by the RFID tag circuit (902) may be used to charge an energy storage capacitor (916) through a current limiting resistor (917). The microcontroller (906) may be configured to control the current flow from the energy storage capacitor (916) through the photo emitter (908) by turning MOSFET transistor (918) on and off. A resistor (919) may limit the current flow through the photo emitter (908) when the MOSFET transistor (918) is turned on, and the value of the resister (919) may be selected to allow at least about 20 milliamps of current to flow in order to produce an output beam from photo emitter (908).

Sensor tag (900) may have circuit components configured to reduce optical or electrical noise or disturbance that may cause an inaccurate reading by the photo detector (910), e.g., by reducing any sub-threshold current, dark currents, offset values intrinsic to any of the electronic components, or by nulling the effect of ambient light. For example, the photo detector (910) may be connected to an operational amplifier (907) which may be configured as a transimpedance amplifier. The gain, bandwidth and delay for the transimpedance amplifier may be determined by the operational amplifier (907) and the passive components (920, 921, 922, 923). The photo detector (910) may be configured to operate in photovoltaic mode, which may help to minimize the variation in its response due to dark current. The output of operational amplifier (907) may be connected to an analog-to-digital input in the microcontroller (906) through a low pass RC network (924, 925). The microcontroller (906) may communicate with the RFID tag circuit (902) and a digital-to-analog converter (909) via a serial peripheral interface. The microcontroller (906) may be configured to set and interrogate any internal registers of the RFID tag circuit (902), which may also be accessible through a radio data communications protocol. The digital-to-analog converter (909) may be adjusted by the microcontroller (906) to provide a bias current to null the effect of ambient light and to compensate for any offset voltages that may be associated with the operational amplifier (907).

Figure 12:
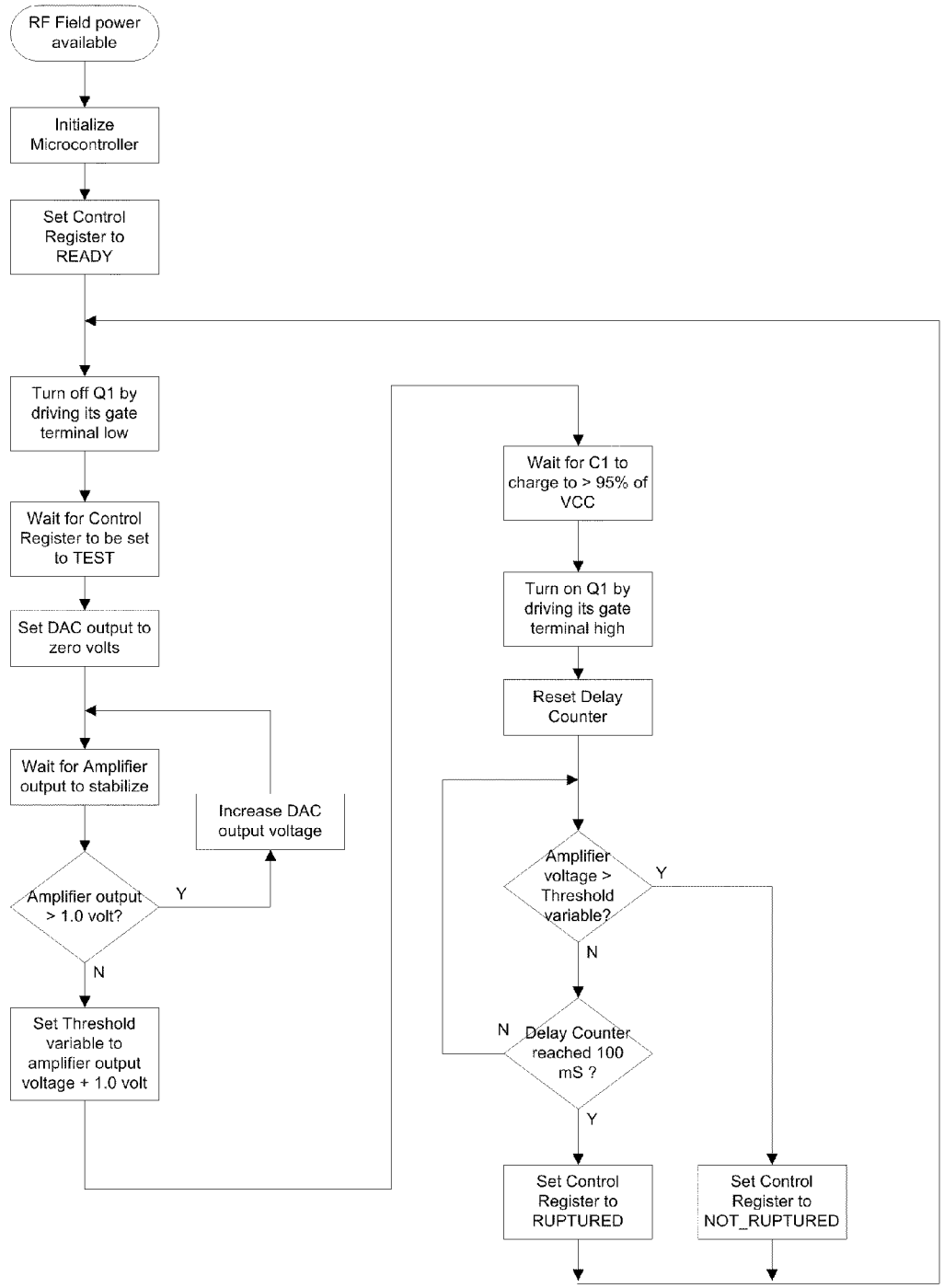
FIG. 12 is a flowchart representation of one example of a sequence of operations that may be performed by a microcontroller of the sensor tag.

FIG. 12 is a flowchart representation showing one example of a sequence of operations that may be performed by the microcontroller (906). Power for the sensor tag (5) may be supplied entirely from the RF field, so the microcontroller (906) may be inoperative until a sufficiently strong RF field is present. When the RF field is present, the microcontroller (906) may be released from its reset state and may begin to execute instructions contained in its flash memory. The instructions may first initialize the microcontroller (906) and its peripheral circuitry. Next, microcontroller (906) may set a control register in the RFID tag circuit (902) to READY, indicating that the sensor tag (900) is ready to perform a test of the implant shell integrity. It may then turn off MOSFET transistor (918) by driving its gate terminal low and may wait until the control register is set to TEST by the implant tag reader (2). The implant tag reader (2) may then confirm the control register in the RFID tag circuit (902) was set to READY via the radio communications interface, and when it is ready to proceed, may set the control register to TEST. Upon detecting that the control register now contains TEST, microcontroller (906) may proceed with the implant test process by setting the digital-to-analog converter (909) to zero volts. If the ambient light level is low, then the current flowing into the cathode of photo detector (910) may also be low, and the output of operational amplifier (907) may be below one volt. On the other hand, if the ambient light level is sufficiently high, then a current may flow into the cathode of photo detector (910) even though the photo emitter (908) has not been excited. This may produce a voltage above one volt at the output of operational amplifier (907). A feedback control algorithm may be used to adjust the output voltage of digital-to-analog converter (909) such that the current it supplies to the summing junction is sufficient to drive the voltage at the output of operational amplifier (907) to approximately one volt. Adjusting the output of operational amplifier (907) to one volt may help ensure that digital-to-analog converter (909) has not supplied excess current to the summing junction, which may cause the output of operational amplifier (907) to saturate against its negative supply rail. The microcontroller (906) next sets its internal threshold variable to a value one volt greater than the voltage measured at the output of operational amplifier (907). With MOSFET transistor (918) switched off, energy storage capacitor (916) may accumulate charge at a rate dependent on the current derived from the RF field. When the voltage across energy storage capacitor (916) exceeds 95% of the VCC voltage, the microcontroller (906) may turn on MOSFET transistor (918), thereby releasing a large current flow through the photo emitter (908). This may produce a high intensity optical pulse that is transmitted through the optical fiber (8) and may be received by the photo detector (910). The microcontroller (906) may wait for 100 milliseconds for the optical pulse to produce a received pulse signal at the input to the internal analog-to-digital converter. If the digitized value exceeds the value of the internal threshold variable set previously, the pulse is considered received and the microcontroller (906) may set the control register in RFID tag circuit (902) to NOT_RUPTURED. If the digitized value fails to exceed the value of the internal threshold variable set previously, the pulse is considered not received and the microcontroller (906) sets the control register in the RFID tag circuit (902) to RUPTURED. After setting the control register, the microcontroller (906) may turn off MOSFET transistor (918) and may wait for the control register to be set to TEST to repeat the test process. If the RF field is removed, then the microcontroller (906) may become inactive once again.

Figure 10:
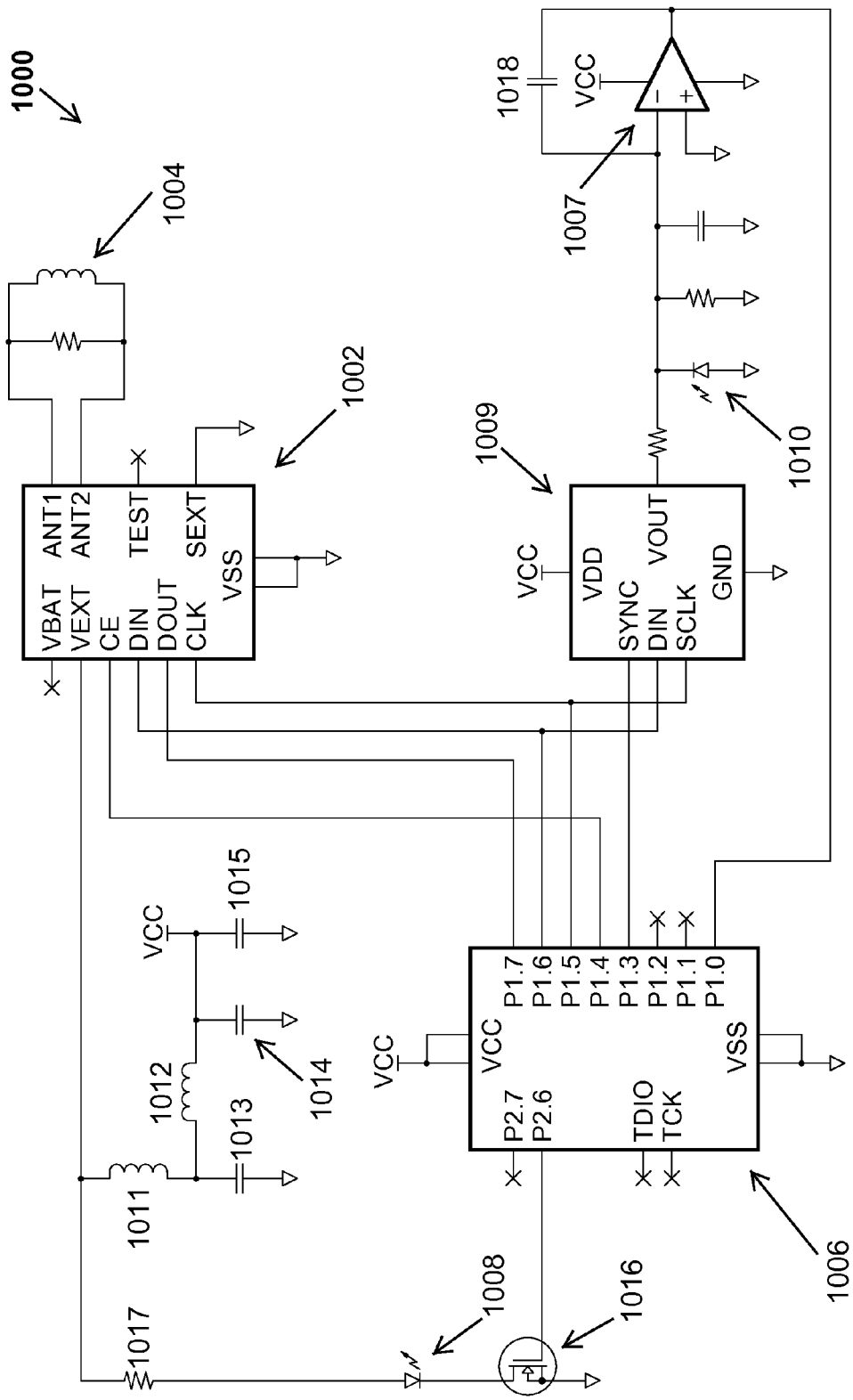
FIG. 10 is schematic diagram of another variation of a sensor tag that may be included with an implantable device.

FIG. 10 depicts an example of a sensor tag where the signal from the photo detector may be integrated over a certain period of time. For example, sensor tag (1000) may be configured to integrate the light signal from the photo detector over a long time period. Sensor tag (1000) may comprise a RFID tag circuit (1002) and an antenna (1004) connected to the RFID tag circuit. The RFID tag circuit (1002) may comprise an integrated circuit with a serial peripheral interface (SPI) and a VEXT terminal that may be used to power additional devices (e.g., an IDS-Microchip SL13A). The antenna (1004) may be a loop antenna that may be used to collect electromagnetic energy, as well as for wireless communications (e.g., radio communications). The loop antenna may have an inductance of about 5.5 micro henries, and may be constructed any suitable method, (e.g., using printed circuit board techniques). The loop antenna and a capacitor inside the RFID tag circuit (1002) may form a tank circuit tuned to 13.56 MHz. The sensor tag (1000) may also comprise a microcontroller (1006), a photo emitter (1008), and a photo detector (1010). The microcontroller (1006) may be any appropriate microcontroller chip, such as Texas Instruments MSP430F2002 and the like. The photo emitter (1008) may be a light-emitting diode that is configured to emit a narrow beam for efficient coupling to the optical fiber (e.g., the bare die form of a Hammamatsu L62896), and may be configured to be driven at a low current level. The photo detector (1010) may be a photodiode, such as a Hamamatsu S1336. The RFID tag circuit (1002) may supply D.C. power for one or more of the components of the sensor tag (1000). For example, the power supplied by the RFID tag circuit (1002) to the microcontroller (1006), the photo detector (1010) and any additional electrical components (e.g., circuitry associated with the photo detector) may be filtered by a low pass LC network (e.g., a low pass LC network comprising 1011, 1012, 1013, 1014, 1015), and is labeled as VCC. Microcontroller (1006) may control the current flow through the photo emitter (1008) by turning MOSFET transistor (1016) on and off. Resistor (1017) limits the current flow through photo emitter (1008) when MOSFET transistor (1016) is turned on.

One example in which the sensor tag (1000) may be configured to integrate the signal from the photo detector (1010) over a period of time is by connecting the photo detector (1010) to an operational amplifier (1007), which may be configured as an integrating amplifier. The photo detector (1010) may be configured to operate in photovoltaic mode, which may help to minimize the variation in its response due to dark current. The output of the operational amplifier (1007) may be connected to an analog-to-digital input in the microcontroller (1006). The microcontroller (1006) may be configured to communicate with the RFID tag circuit (1002) and digital-to-analog converter (1009) via a serial peripheral interface. The microcontroller (1006) may be configured to set and interrogate registers within the RFID tag circuit (1002), which may also accessible through the radio data communications protocol. The digital-to-analog converter (1009) may be adjusted by the microcontroller (1006) to provide a bias current to null the effect of ambient light and to compensate for offset voltages associated with the operational amplifier (907).

Figure 13:
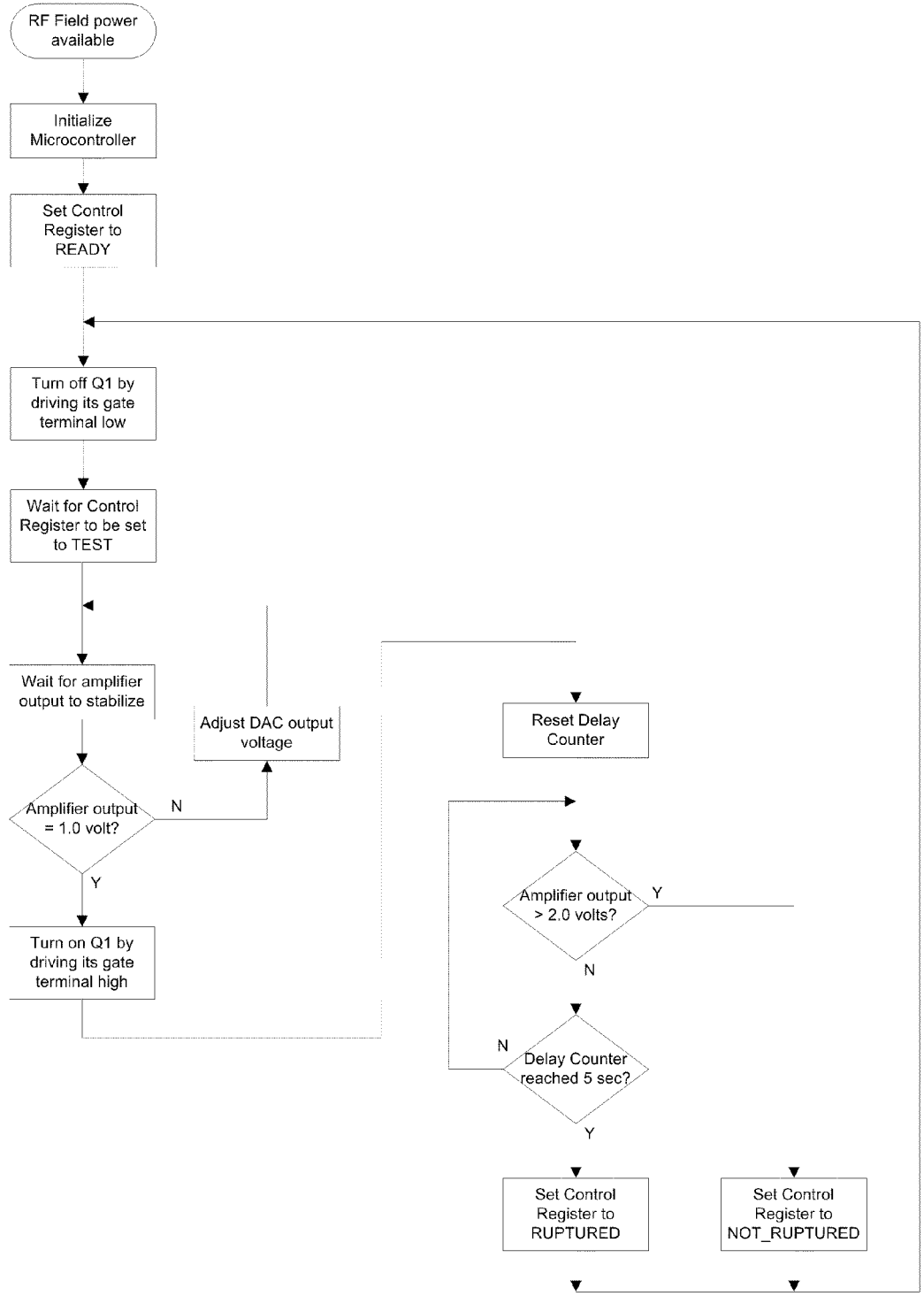
FIG. 13 is a flowchart representation of another example of a sequence of operations that may be performed by a microcontroller of a sensor tag.

FIG. 13 is a flowchart showing one example of a sequence of operations that may be performed by the microcontroller (1006) of the sensor tag (1000). Power for the sensor tag (1000) may be supplied entirely from the RF field, so the microcontroller (1006) is inoperative until a sufficiently strong RF field is present. When the RF field is present, the microcontroller (1006) may be released from its reset state and begins to execute instructions contained in its flash memory. The instructions may first initialize the microcontroller (1006) and its peripheral circuitry. Next, the microcontroller (1006) may set a control register in the RFID tag circuit (1002) to READY, indicating that the sensor tag (1000) is ready to perform a test of the implant shell integrity. It may then turn off MOSFET transistor (1016) by driving its gate terminal low and may wait until the control register is set to TEST by the implant tag reader (2). Implant tag reader (2) may confirm that the control register in the RFID tag circuit (1002) was set to READY via the radio communications interface and when it is ready to proceed, may set the control register to TEST. Upon detecting that the control register now contains TEST, the microcontroller (1006) may proceed with the implant test process by adjusting the digital-to-analog converter (1009) using a feedback control algorithm such that the voltage at the output of operational amplifier (1007) is within approximately 100 millivolts of one volt. This adjustment may compensate for current produced by photo detector (1010) due to the presence of ambient light. MOSFET transistor (1016) may be switched on, which may cause the photo emitter (1008) to inject photons into the optical fiber, which may be received by the photo detector (1010), which may produce current levels of a few microamperes. The operational amplifier accumulates the low current level by charging integrating capacitor (1018) and producing an increasing voltage at the output of operational amplifier (1007). The microcontroller (1006) may wait for up to five seconds for the voltage at the output of operational amplifier (1007) to exceed two volts. If the measured voltage exceeds two volts, the microcontroller (1006) may set the control register in RFID tag circuit (1002) to NOT_RUPTURED. If the measured value fails to exceed two volts, the microcontroller (1006) may set the control register in RFID tag circuit (1002) to RUPTURED. After setting the control register, the microcontroller (1006) may turn off MOSFET transistor (1016) and wait for the control register to be set to TEST to repeat the test process. If the RF field is removed, then the microcontroller (1006) may become inactive again.

Figure 11:
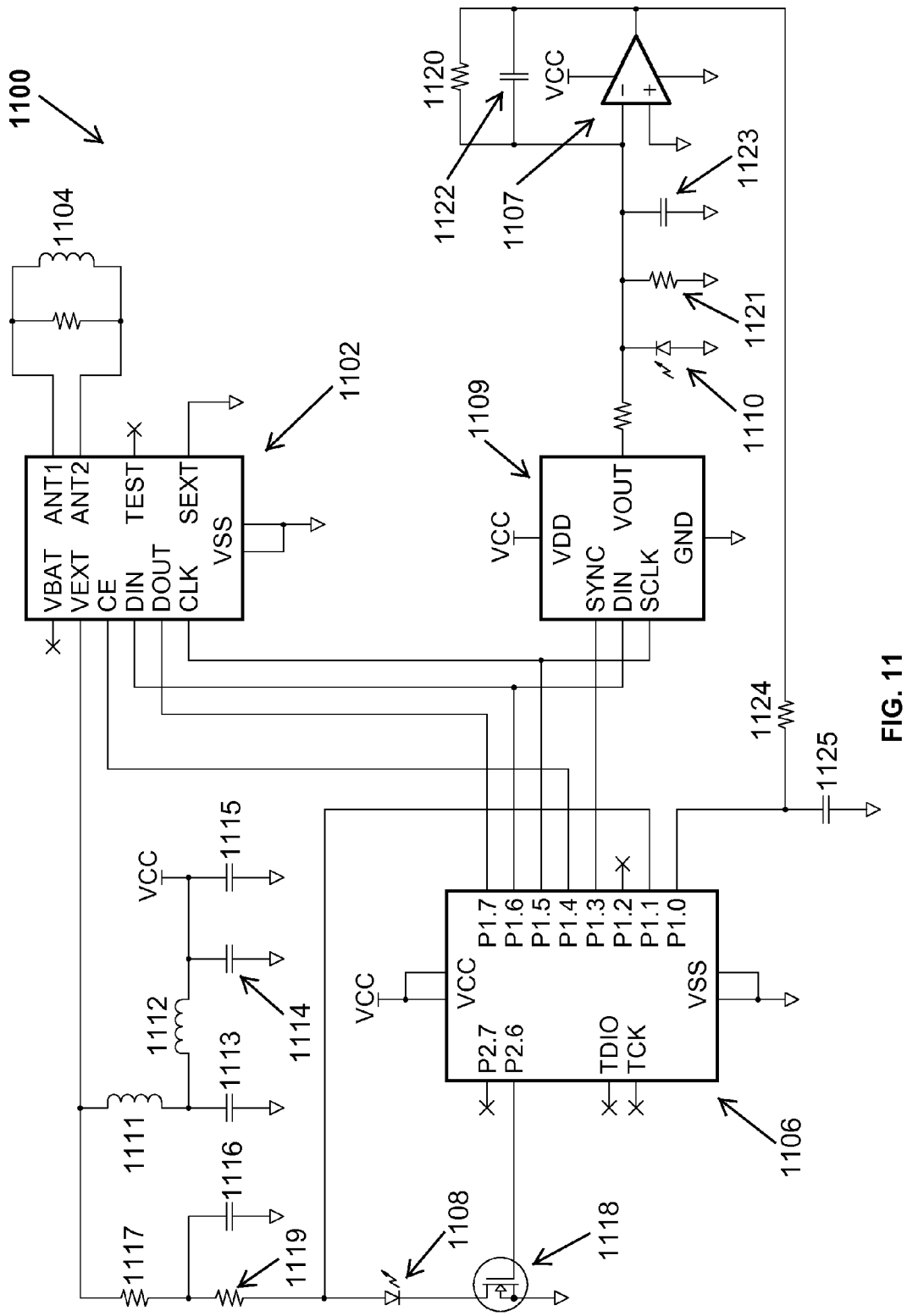
FIG. 11 is schematic diagram of another variation of a sensor tag that may be included with an implantable device.

FIG. 11 depicts an example of a sensor tag where the photo emitter may be driven on and off, e.g., at 8 Hz, which may produce a fluctuating signal from the photo detector. The fluctuating signal may be amplified and demodulated to detect a rupture. Sensor tag (1100) may comprise a RFID tag circuit (1102) and an antenna (1104) may be connected to the RFID tag circuit. The RFID tag circuit (1102) may comprise an integrated circuit with a serial peripheral interface (SPI) and a VEXT terminal that may be used to power additional devices (e.g., an IDS-Microchip SL13A). The antenna (1104) may be a loop antenna that may be used to collect electromagnetic energy, as well as for wireless communications (e.g., radio communications). The loop antenna may have an inductance of about 5.5 micro henries, and may be constructed any suitable method, (e.g., using printed circuit board techniques). The loop antenna and a capacitor inside the RFID tag circuit (1102) may form a tank circuit tuned to 13.56 MHz. The sensor tag (1100) may also comprise a microcontroller (1106), a photo emitter (1108), and a photo detector (1110). The microcontroller (1106) may be any appropriate microcontroller chip, such as Texas Instruments MSP430F2002 and the like. The photo emitter (1108) may be a light-emitting diode that is configured to emit a narrow beam for efficient coupling to the optical fiber (e.g., the bare die form of a Hammamatsu L62896). The photo detector (1110) may be a photodiode, such as a Hamamatsu S1336. The RFID tag circuit (1102) may supply D.C. power for one or more of the components of the sensor tag (1100). For example, the power supplied by the RFID tag circuit (1102) to the microcontroller (1106), the photo detector (1110) and any additional electrical components (e.g., circuitry associated with the photo detector) may be filtered by a low pass LC network (e.g., a low pass LC network comprising 1111, 1112, 1113, 1114, 1115), and is labeled as VCC. Unfiltered power supplied by the RFID tag circuit (1102) may be used to charge an energy storage capacitor (1116) through a current limiting resistor (1117). The microcontroller (1106) may be configured to control the current flow from the energy storage capacitor (1116) through the photo emitter (1108) by turning MOSFET transistor (1118) on and off. Resistor (1119) limits the current flow through the photo emitter (1108) when MOSFET transistor (1118) is turned on.

Sensor tag (1100) may have circuit components configured to reduce optical or electrical noise or disturbance that may cause an inaccurate reading by the photo detector (1110), e.g., by reducing any sub-threshold current, dark currents, offset values intrinsic to any of the electronic components, or by nulling the effect of ambient light. For example, the photo detector (1110) may be connected to an operational amplifier (1107) which may be configured as a transimpedance amplifier. The gain, bandwidth and delay for the transimpedance amplifier may be determined by the operational amplifier (1107) and the passive components (1120, 1121, 1122, 1123). The photo detector (1110) may be configured to operate in photovoltaic mode, which may help to minimize the variation in its response due to dark current. The output of operational amplifier (1107) may be connected to an analog-to-digital input in the microcontroller (1106) through a low pass RC network (1124, 1125). The microcontroller (1106) may communicate with the RFID tag circuit (1102) and a digital-to-analog converter (1109) via a serial peripheral interface bus. The microcontroller (1106) may be configured to set and interrogate any internal registers of the RFID tag circuit (102), which may also accessible through a radio data communications protocol. The digital-to-analog converter (1109) may be adjusted by the microcontroller (1106) to provide a bias current to null the effect of ambient light and to compensate for offset voltages associated with operational amplifier (1107).

Figure 14:
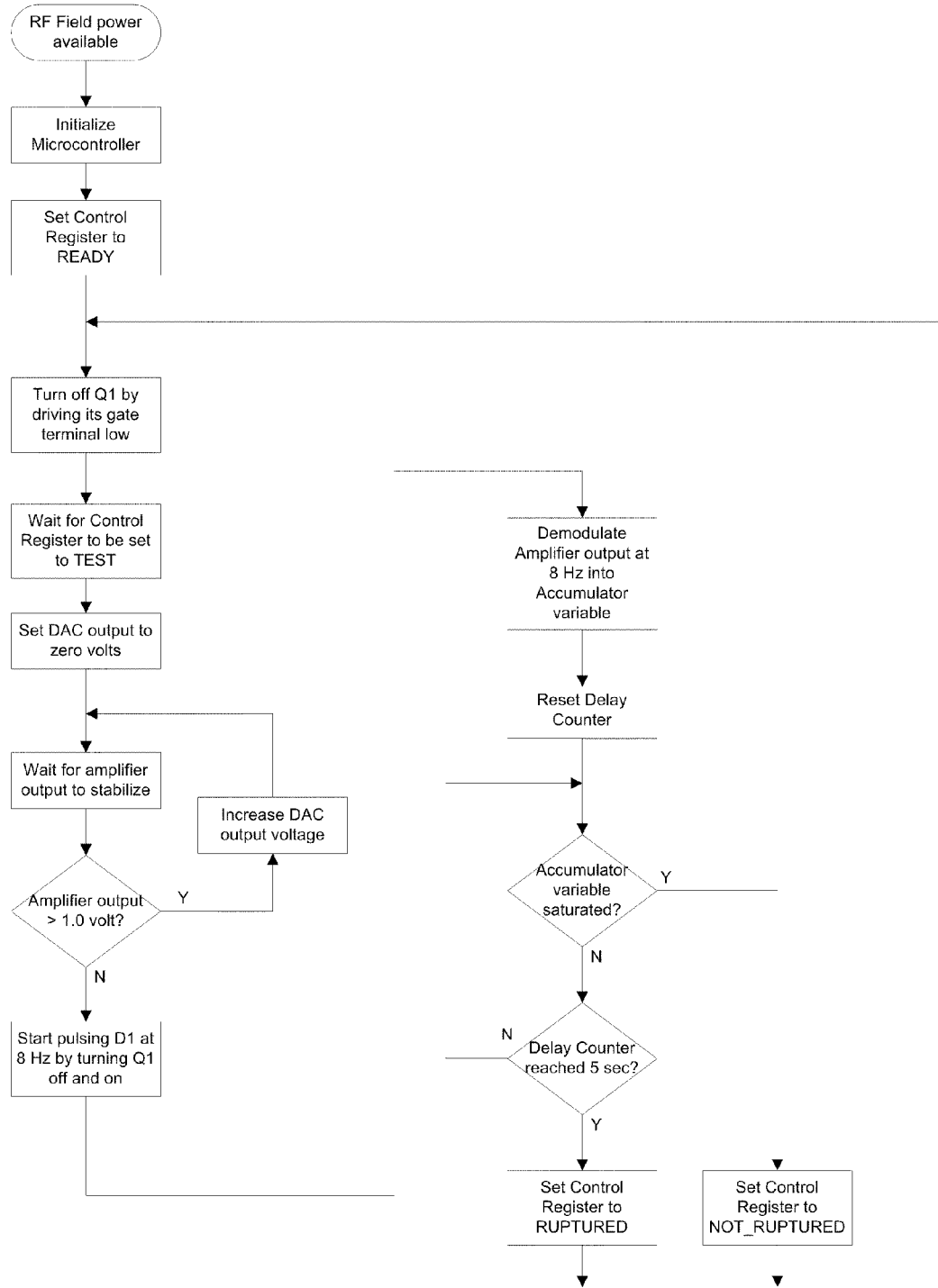
FIG. 14 is a flowchart representation of another example of a sequence of operations that may be performed by a microcontroller of a sensor tag.

FIG. 14 is a flowchart showing one example of a sequence of operations that may be performed by the microcontroller (1106) of the sensor tag (1100). Power for the sensor tag (1100) may be supplied entirely from the RF field, so the microcontroller (1106) may be inoperative until a sufficiently strong RF field is present. When the RF field is present, the microcontroller (1106) may be released from its reset state and may begin to execute instructions contained in its flash memory. The instructions may first initialize the microcontroller (1106) and its peripheral circuitry. Next, the microcontroller (1106) may set a control register in the RFID tag circuit (1102) to READY, indicating that the sensor tag (1100) is ready to perform a test of the implant shell integrity. It then may turn off MOSFET transistor (1118) by driving its gate terminal low and may wait until the control register is set to TEST by implant tag reader (2). Implant tag reader (2) may confirm that the control register in the RFID tag circuit (1102) was set to READY, via the radio communications interface and when it is ready to proceed, sets the control register to TEST. Upon detecting that the control register now contains TEST, the microcontroller (1106) may proceed with the implant test process by setting the digital-to-analog converter (1109) to zero volts. If the ambient light level is low, then the current flowing into the cathode of the photo detector (1109) may also be low, and the output of operational amplifier (1107) may be below one volt. On the other hand, if the ambient light level is sufficiently high, then a current may flow into the cathode of photo detector (1110) even though the photo emitter (1108) has not been turned on, which may produce a voltage above one volt at the output of operational amplifier (1107). A feedback control algorithm may be employed to adjust the output voltage of digital-to-analog converter (1109) such that the current it supplies to the summing junction is sufficient to drive the voltage at the output of operational amplifier (1107) to approximately one volt. Adjusting the output of operational amplifier (1107) to one volt, may help ensure that digital-to-analog converter (1009) has not supplied excess current to the summing junction which may cause the output of operational amplifier (1107) to saturate against its negative supply rail. With MOSFET transistor (1118) switched off, energy storage capacitor (1116) may accumulate charge at a rate dependent on the current derived from the RF field. When the voltage across energy storage capacitor (1116) exceeds 95% of the VCC voltage, the microcontroller (1106) starts turning MOSFET transistor (1118) off and on using a pulse-width modulation circuit contained within the microcontroller (1106). This may produce a fluctuating optical signal that is sent through the optical fiber and may be received by the photo detector (1110). The microcontroller (1106) may digitally demodulate this signal and may add the result to an accumulator variable. If the value for the accumulator saturates its numerical representation, the signal may be considered received and the microcontroller (1106) may set the control register in RFID tag circuit (1102) to NOT_RUPTURED. If after five seconds, the value for the accumulator fails to saturate its numerical representation, the signal may be considered not received and the microcontroller (1106) may set the control register in RFID tag circuit (1102) to RUPTURED. After setting the control register, the microcontroller (1106) may turn off MOSFET transistor (Q1) and may wait for the control register to be set to TEST to repeat the test process. If the RF field is removed, then the microcontroller (1106) may become inactive again.

While non-invasive rupture detection systems using a single waveguide such as a silicone optical fiber have been described above, some rupture detection systems may use a single strand of flexible, electrically conductive material such as, a small diameter copper wire, or electrically conductive polymer. A rupture in the implant shell may cause a corresponding rupture in the copper wire or conductive polymer.

Figure 15:
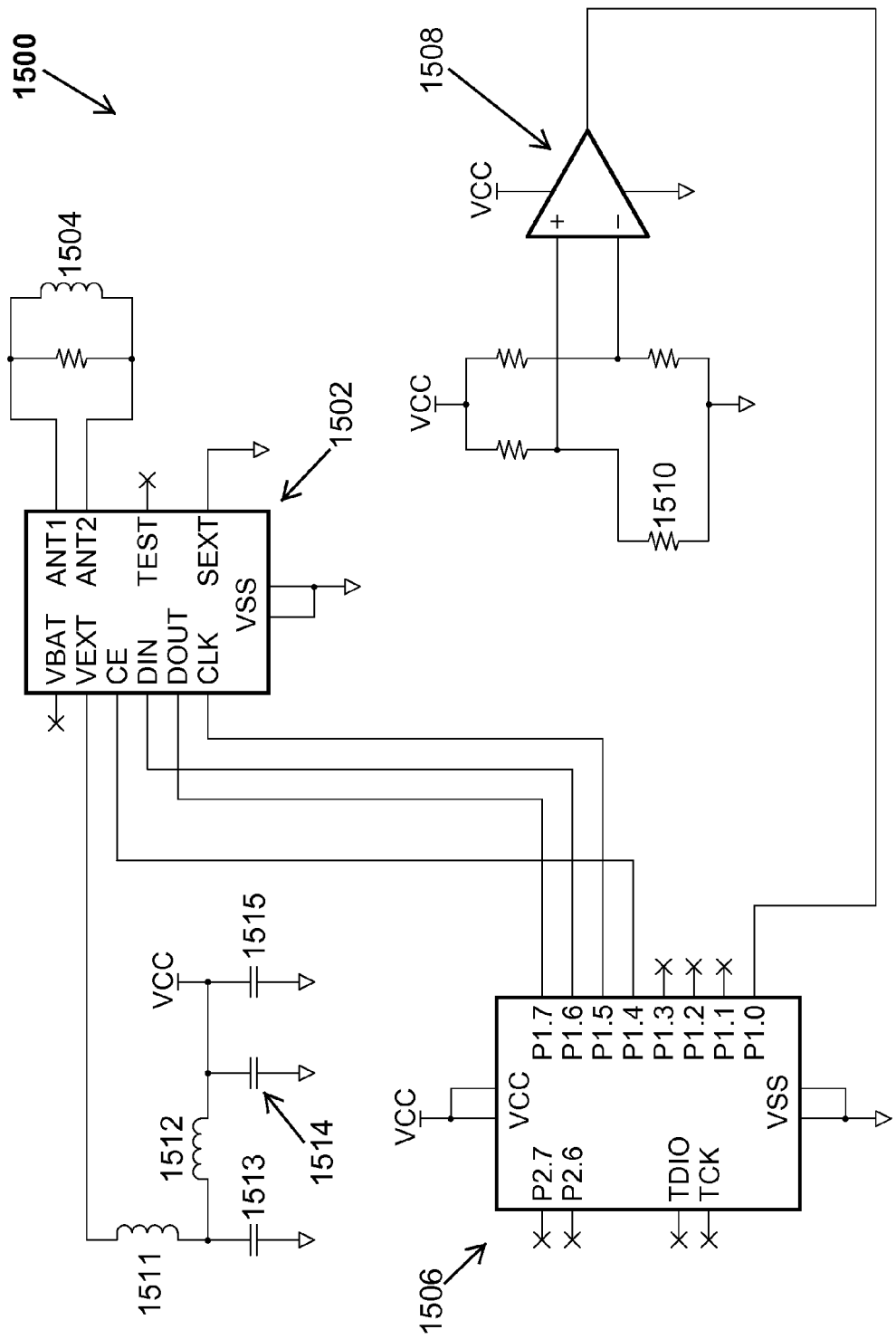
FIG. 15 is schematic diagram of another variation of a sensor tag that may be included in an implantable device.

FIG. 15 depicts one variation of a sensor tag (1500) that may be used with a conductive material to detect a rupture in the shell of an implant. The sensor tag (1500) may comprise a RFID tag circuit (1502) and an antenna (1504) connected to the RFID tag circuit. The RFID tag circuit (1502) may comprise an integrated circuit with a serial peripheral interface (SPI) and a VEXT terminal that may be used to power additional devices (e.g., an IDS-Microchip SL13A). The antenna (1504) may be a loop antenna that may be used to collect electromagnetic energy, as well as for wireless communications (e.g., radio communications). The loop antenna may have an inductance of about 5.5 micro henries and may be constructed any suitable method, (e.g., using printed circuit board techniques). The loop antenna and a capacitor inside the RFID tag circuit (1502) may form a tank circuit tuned to 13.56 MHz. The sensor tag (1500) may also comprise a microcontroller (1506), where the microcontroller may be any appropriate microcontroller chip, such as Texas Instruments MSP430F2002 and the like. The RFID tag circuit (1502) may supply D.C. power for one or more of the components of the sensor tag (1500), which may be filtered by the low pass LC network (1511, 1512, 1513, 1514, 1515), and labeled as VCC. The output of a comparator (1508) may swing to a logic low level when the voltage at its negative input is greater than the voltage at its positive input and may swing to a logic high level when the voltage at its positive input is greater than the voltage at its negative input. The voltage at the negative input of the comparator (1508) may be fixed at approximately ½ of VCC. When the conductive material forming a rupture sensor (1510) is intact, it may have a resistance less than five megaohms which may cause the voltage on the positive input of the comparator (1508) to be less than ⅓ of VCC which causes the its output to swing to a logic low level. If the conductive material forming the rupture sensor (1510) is broken the positive input of the comparator (1508) may be pulled to VCC and its output may swing to a logic high level. The output of comparator (1508) may be connected to an input port on the microcontroller (1506) which may perform handshaking communications through RFID tag circuit (1502) to coordinate testing operations and to relay the results of the test to an external implant tag reader.

One method of manufacturing an implant shell with a single strand of an electrically conductive material as described above may comprise applying a uniform coating or layer made of a conductive material (e.g., a conductive silicone), removing a circuitous path to form a single ribbon or trace of conductive material. The single ribbon or trace of conductive material may be distributed across the implant shell such that it spans the surface of the shell. The conductive material may then be removed by laser scribe or photochemical etch or another process. With this approach, the implant rupture sensor is formed as part of the manufacturing process for the implant shell (3), which may reduce the need for additional components, and may simplify the handling of delicate parts.

One example of a method of detecting a rupture in a breast implant using any of the non-invasive rupture detection systems described above may comprise holding the RFID tag reader in proximity to initiate communication with the implanted sensor tag, sending a wireless command from the RFID tag reader to the sensor tag to initiate a test of prosthetic breast implant, and reading out the results of the test. The RFID tag reader may initiate a test of the implant by transmitting an electromagnetic signal to set a control register of the sensor tag. The sensor tag may return a value reflective of the status of the shell. Performing a test may comprise sending a wireless command to the implanted sensor tag, pulsing the photo emitter to produce a burst of light transmitted through the single optical fiber, and detecting any light transmitted through the optical fiber by the photo detector. The status indicated by the presence or absence of the light from the emitter and detected by the photo detector may be sent back to the RFID tag reader via wireless communication, where the implant rupture status indication may be presented to the medical practitioner.

The implant rupture detection system may be activated or used prior to surgical implantation of the prosthetic breast implant to confirm that the communications and rupture detection mechanisms are working properly. It may also be used during installation of the implant to ensure that the implant was not ruptured during the surgical procedure, for example, as a result of implant deformation during insertion or contact with surgical instrumentation. It may also be used to perform routine, periodic confirmations of the integrity of the implant while implanted in a patient, with or without the use of MRI.

The instructions coded into the flash memory of the microcontroller contained in the implant may be modified to adjust the test procedure or rupture detection criteria. The microcontroller may be configured to download revisions to the software wirelessly via the RFID communications circuitry. This may allow software updates to be applied prior to or after implantation.

A kit that may be provided for a prosthetic breast implant surgery may comprise a prosthetic breast implant with a silicone shell, a sensor tag embedded in the silicone shell, a single silicone optical fiber embedded in the silicone shell and coupled to the sensor tag, and an external sensor tag reader configured to wirelessly communication with the sensor tag. Optionally, the kit may also comprise an instruction manual and one or more peripheral data devices (e.g., router, pager, radio transmitter, etc.).

The non-invasive rupture detection systems described herein may also be applied to remote or inaccessible pipes, tubes or tanks containing dangerous toxic or explosive materials. The rupture detector may comprise a single, electrically conductive wire distributed across the inner or outer surface of a cylindrical pipe, tube or tank and covered with a tough coating (e.g., a thick epoxy coating). An optical waveguide as described above may also be used. If the electrically conductive wire is broken as reflected by a reduction of an electrical current or an increase in impedance, then the pipe, tube or tank may be considered to be ruptured, fractured or broken. For example, the electrically conductive wire (e.g., an insulated magnet wire) may be distributed across a cylindrical pipe section in a helical pattern starting at one end. At the other end of the pipe section, the helix may be advanced in the opposite direction which may form a diamond like pattern of electrically conductive wire across the surface of the cylinder. The spacing of the electrically conductive wire may determine the size of the rupture the sensor can detect. The ends of the electrically conductive wire may be connected to an electronic circuit that measures the resistance of the electrically conductive wire to determine whether it has been broken. The electronic circuit may be connected to other wired or wireless communications devices or networks to report the rupture status of the pipe section and the entire pipeline. The rupture detection system may also be applied across couplings or other devices to determine whether a breach has occurred.

The rupture detection systems described herein may also be used in fixed structures or vehicles of many types, for example, for the detection of a breach in the surface of space vehicles, aircraft exteriors, ships hulls, armored vehicles, etc. The rupture detector may comprise a single, electrically conductive wire distributed across and bonded to the inner or outer surface of a section of a vehicle or structure. If the electrically conductive wire is broken such that it no longer conveys an electrical current, the section of the vehicle or structure is considered to have been breached. The ends of each electrically conductive wire for each section are connected to a central monitoring device which may determine the conductivity of the electrically conductive wires and may report the rupture or failure status of the vehicle or structure.

The rupture detection system described herein may also be included in fumigation tarps. Fumigation tarps may be placed on and around structures to contain highly poisonous, gaseous insecticides while eradicating harmful or destructive pests. If the tarps are torn or cut, the concentration of poisonous gas may drop to an ineffective level or may pose a hazard outside the tarped structure. A single, flexible electrically conductive wire may be woven into the fabric of the fumigation tarp and coated with a polymer sealant. If the electrically conductive wire is broken such that it no longer conveys an electrical current, the tarp may be considered to have been breached and the fumigation process compromised. The ends of each electrically conductive wire may be connected to an electronic circuit which may report the rupture status of each tarp to a central monitoring device via a short range wireless communications link.

Rupture detection systems may also be applied to sails or inflated, lighter-than air vehicles, such as sailboat sails, hot air balloons, and the like. The rupture detector may comprise a single, flexible electrically conductive wire woven into the sail cloth or balloon fabric. If the electrically conductive wire is broken such that it no longer conveys electrical current, the fabric may be considered to have been breached. When the sail or balloon fabric is repaired, a light fabric patch with electrically conductive wire woven into it is affixed across the tear and the electrical conductive wire is spliced into the circuit to restore the rupture detection capability.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected by Letters Patent of the United States is:

1. A rupture detection system comprising:
    a photo emitter;
    a photo detector;
    a single optical waveguide between the photo emitter and the photo detector, wherein the photo emitter is configured to emit an optical signal through the waveguide, and wherein the photo detector is configured to provide an indication of receipt of the optical signal to detect a discontinuity in the optical waveguide, and wherein the optical waveguide is configured to break when a shell of a breast implant is subjected to mechanical stresses that will eventually lead to its rupture; and
    a radio frequency identification (RFID) circuit in communication with the photo emitter and photo detector, wherein the RFID circuit is configured to issue commands to the photo emitter and to wirelessly transmit the indicator from the photo detector to a RFID reader, and wherein the photo emitter, photo detector, optical waveguide, and RFID circuit are attached to the shell of the breast implant.

2. The rupture detection system of claim 1, wherein the optical waveguide is made of a material having mechanical properties of the shell of the breast implant such that the optical waveguide will break when the shell ruptures.

3. The rupture detection system of claim 2, wherein the optical waveguide is a silicone-based optical fiber.

4. The rupture detection system of claim 3, wherein the single optical fiber is distributed across the shell.

5. The rupture detection system of claim 4, wherein the single optical fiber is distributed across the shell such that the optical fiber does not cross itself more than twice.

6. The rupture detection system of claim 4, wherein the single optical fiber is distributed across the shell in two or more separate layers of the shell.

7. The rupture detection system of claim 1, wherein the photo detector comprises a noise reduction sub-circuit.

8. The rupture detection system of claim 7, wherein the noise reduction sub-circuit is configured to reduce noise that originates in circuitry of the photo detector.

9. The rupture detection system of claim 6, wherein the photo detector has a dark current, and wherein the noise reduction sub-circuit reduces a bias in the photo detector by compensating for the dark current.

10. The rupture detection system of claim 6, wherein the noise reduction sub-circuit is configured to reduce noise that is present in the single optical waveguide.

\* \* \* \* \*